United States Patent
Julia Jane et al.

(10) Patent No.: US 9,562,039 B2
(45) Date of Patent: Feb. 7, 2017

(54) SALTS OF 2-AMINO-1-HYDROXYETHYL-8-HYDROXYQUINOLIN-2(1H)-ONE DERIVATIVES HAVING BOTH β2 ADRENERGIC RECEPTOR AGONIST AND M3 MUSCARINIC RECEPTOR ANTAGONIST ACTIVITIES

(71) Applicant: ALMIRALL, S.A., Barcelona (ES)

(72) Inventors: Montserrat Julia Jane, Barcelona (ES); Francesc Carrera Carrera, Barcelona (ES); Maria Prat Quiñones, Barcelona (ES); Carlos Puig Duran, Barcelona (ES); Francesca Pajuelo Lorenzo, Barcelona (ES); Juan Antonio Perez Andres, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 14/770,206

(22) PCT Filed: Feb. 27, 2014

(86) PCT No.: PCT/EP2014/053871
§ 371 (c)(1),
(2) Date: Aug. 25, 2015

(87) PCT Pub. No.: WO2014/131851
PCT Pub. Date: Sep. 4, 2014

(65) Prior Publication Data
US 2016/0009698 A1    Jan. 14, 2016

Related U.S. Application Data

(60) Provisional application No. 61/804,558, filed on Mar. 22, 2013.

(30) Foreign Application Priority Data

Feb. 27, 2013   (EP) .................................... 13382060

(51) Int. Cl.
| | | |
|---|---|---|
| *C07D 409/14* | (2006.01) | |
| *A61K 31/4709* | (2006.01) | |
| *A61K 45/06* | (2006.01) | |
| *A61K 9/00* | (2006.01) | |
| *C07C 59/255* | (2006.01) | |
| *C07C 309/05* | (2006.01) | |
| *C07D 275/06* | (2006.01) | |

(52) U.S. Cl.
CPC ........... *C07D 409/14* (2013.01); *A61K 9/0073* (2013.01); *A61K 9/0075* (2013.01); *A61K 31/4709* (2013.01); *A61K 45/06* (2013.01); *C07C 59/255* (2013.01); *C07C 309/05* (2013.01); *C07D 275/06* (2013.01); *C07B 2200/13* (2013.01)

(58) Field of Classification Search
CPC ... C07D 275/06; C07D 409/14; C07C 309/05; C07C 59/255; C07B 2200/13; A61K 31/4709; A61K 9/0073; A61K 9/0075; A61K 45/06
See application file for complete search history.

(56) References Cited

U.S. PATENT DOCUMENTS

| | | |
|---|---|---|
| 4,556,653 A | 12/1985 | Giani et al. |
| 5,397,800 A | 3/1995 | Alker et al. |
| 6,673,908 B1 | 1/2004 | Stanton, Jr. |
| 9,072,734 B2 | 7/2015 | Mitsuyama et al. |
| 9,233,108 B2 | 1/2016 | Aiguade Bosch et al. |
| 9,315,463 B2 | 4/2016 | Prat Quinones et al. |
| 2012/0046467 A1 | 2/2012 | Mitsuyama et al. |
| 2013/0053359 A1 | 2/2013 | Prat Quinones et al. |
| 2013/0281415 A9 | 10/2013 | Prat Quinones et al. |
| 2014/0303127 A1 | 10/2014 | Bosch et al. |
| 2014/0378421 A1 | 12/2014 | Bosch et al. |
| 2015/0329535 A1 | 11/2015 | Sole Feu et al. |
| 2016/0015704 A1 | 1/2016 | Aparici Virgili et al. |
| 2016/0143915 A1 | 5/2016 | Aiguade Bosch et al. |
| 2016/0166566 A1 | 6/2016 | Julia Jane et al. |
| 2016/0175295 A1 | 6/2016 | Aparici Virgili et al. |
| 2016/0200718 A1 | 7/2016 | Aiguade Bosch et al. |

FOREIGN PATENT DOCUMENTS

| | | |
|---|---|---|
| CN | 101544572 A | 9/2009 |
| EP | 0147475 | 10/1985 |
| EP | 1 078 629 | 2/2001 |
| EP | 1 894 568 | 3/2008 |
| EP | 2 386 555 | 11/2011 |
| EP | 2386555 | * 11/2011 |
| EP | 2 426 121 | 3/2012 |
| EP | 2 592 077 | 5/2013 |
| EP | 2 592 078 | 5/2013 |
| WO | WO 98/09632 | 3/1998 |
| WO | WO 99/30703 | 6/1999 |

(Continued)

OTHER PUBLICATIONS

U.S. Appl. No. 13/697,060, filed Nov. 9, 2012.
U.S. Appl. No. 14/357,344, filed May 9, 2014.
U.S. Appl. No. 14/357,400, filed May 9, 2014.
U.S. Appl. No. 14/653,048, filed Jun. 17, 2015.
U.S. Appl. No. 14/770,200, filed Aug. 27, 2015.
U.S. Appl. No. 14/956,767, filed Dec. 2, 2015.
U.S. Appl. No. 14/956,836, filed Dec. 2, 2015.
International Search Report, PCT/EP2012/072309, Dec. 18, 2012.
International Search Report PCT/EP2012/072311, Dec. 10, 2012.
International Search Report PCT/EP2011/002376, Aug. 1, 2011.
International Search Report PCT/EP2013/076973, Mar. 11, 2014.

(Continued)

*Primary Examiner* — D M Seaman
(74) *Attorney, Agent, or Firm* — Finnegan, Henderson, Farabow, Garrett & Dunner, LLP

(57) ABSTRACT

The present invention is directed to crystalline addition salts of (i) 8-hydroxyquinolin-2(1H)-one derivatives and (ii) a hydroxycarboxylic acid, a sulfonic acid or a sulfimide, or a pharmaceutically acceptable solvates thereof.

11 Claims, 17 Drawing Sheets

(56) References Cited

FOREIGN PATENT DOCUMENTS

| WO | WO 01/14339 | | 3/2001 |
|---|---|---|---|
| WO | WO 2004/074246 | | 9/2004 |
| WO | WO 2004/074276 | | 9/2004 |
| WO | WO 2004/074812 | | 9/2004 |
| WO | WO 2004/089892 | | 10/2004 |
| WO | WO 2004/106333 | | 12/2004 |
| WO | WO 2005/080375 | | 9/2005 |
| WO | WO 2005/111004 | | 11/2005 |
| WO | WO2005/123693 | A1 | 12/2005 |
| WO | WO 2006/023454 | | 3/2006 |
| WO | WO 2006/023457 | | 3/2006 |
| WO | WO 2006/023460 | | 3/2006 |
| WO | WO 2007/017670 | | 2/2007 |
| WO | WO 2007/090859 | | 8/2007 |
| WO | WO 2007/107828 | | 9/2007 |
| WO | WO 2008/000483 | | 1/2008 |
| WO | WO 2008/017824 | | 2/2008 |
| WO | WO 2008/017827 | | 2/2008 |
| WO | WO 2008/041095 | | 4/2008 |
| WO | WO 2008/087437 | | 7/2008 |
| WO | WO 2008/096127 | | 8/2008 |
| WO | WO 2008/096129 | | 8/2008 |
| WO | WO 2008/149110 | | 12/2008 |
| WO | WO 2009/013244 | | 1/2009 |
| WO | WO 2009/017813 | | 2/2009 |
| WO | WO 2009/098448 | | 8/2009 |
| WO | WO 2009/139709 | | 11/2009 |
| WO | WO 2010/004517 | | 1/2010 |
| WO | WO 2010/015792 | | 2/2010 |
| WO | WO 2010/069504 | A1 | 6/2010 |
| WO | WO 2010/123766 | | 10/2010 |
| WO | WO 2011/012897 | | 2/2011 |
| WO | 2011141180 | * | 11/2011 |
| WO | WO 2011/141180 | A1 | 11/2011 |
| WO | WO 2012/044825 | | 4/2012 |
| WO | WO 2012/085582 | | 6/2012 |
| WO | WO 2012/085583 | | 6/2012 |
| WO | WO 2012/168349 | | 12/2012 |
| WO | WO 2012/168359 | | 12/2012 |
| WO | WO 2013/068552 | | 5/2013 |
| WO | WO 2013/068554 | | 5/2013 |
| WO | WO2013/068875 | | 5/2013 |
| WO | WO2013/071009 | A1 | 5/2013 |
| WO | WO2013/071169 | A1 | 5/2013 |
| WO | WO 2014/086924 | | 6/2014 |
| WO | WO 2014/086927 | | 6/2014 |
| WO | WO 2014/095920 | | 6/2014 |
| WO | WO 2014/131851 | | 9/2014 |
| WO | WO 2014/131852 | | 9/2014 |
| WO | WO 2015/011244 | | 1/2015 |
| WO | WO 2015/011245 | | 1/2015 |
| WO | WO 2016/046390 | | 3/2016 |

OTHER PUBLICATIONS

International Search Report PCT/EP2014/053874, Apr. 17, 2014.
International Search Report PCT/EP2014/065966, Aug. 19, 2014.
International Search Report PCT/EP2014/065965, Sep. 18, 2014.
Barnes, Peter J., "Airway Pharmacology," Textbook of Respiratory Medicine, 3rd Edition, Chapter 11, 2000, pp. 267-272.
Glossop, Paul A. et al., "Progress in the Development of Inhaled, Long-Acting β2-Adrenoceptor Agonists," Annual Reports in Medicinal Chemistry, vol. 41, 2006, pp. 237-248.
Hoffman, Brian B. "Catecholamines, Sympathomimetic Drugs, and Adrenergic Receptor Antagonists," Goodman & Gilman's The Pharmacological Basis of Therapeutics 10$^{th}$ Edition, Chapter 10, pp. 215-232, 2001.
Hughes, Adam et al., Dual-pharmacology Muscarinic Antagonist and β2 Agonist Molecules for the Treatment of Chronic Obstructive Pulmonary Disease, Future Med. Chem., (2011), 3(13), pp. 1585-1605.
Jacobsen, John R., "Third-generation Long-Acting β2 Adrenoceptor Agonists: Medicinal Chemistry Strategies Employed in the Identification of Once-Daily Inhaled β2-Adrenoceptor Agonists," Future Med Chem., 2011, 3(13), pp. 1607-1622.
Naito, Roy et al., "Synthesis and Antimuscarinic Properties of Quinuclidin-3-yl 1,2,3,4-Tetrahydroisoquinoline-2-carboxylate Derivatives as Novel Muscarinic Receptor Antagonists," J. Med Chem., 2005, 48, pp. 6597-6606.
Van Noord, J.A., "Comparison of tiotropium once Daily, Formoterol Twice Daily and Both Combined Once Daily in Patients with COPD," European Respiratory Journal, vol. 26, No. 2., pp. 214-222, 2005.
Bateman, E.D., "Pharmacodynamics of GSK961081, a bi-functional molecule, in patients with COPD," Pulmonary Pharmacology & Therapeutics, vol. 26, pp. 581-587 (2013).
Hughes, A.D. et al., "Multivalent Dual Pharmacology Muscarinic Antagonist and β2 Agonist (MABA) Molecules for the Treatment of COPD, Progress in Medicinal Chemistry," vol. 51, pp. 71-95 (2012).
Hughes, A.D. "Discovery of Muscarinic Acetylcholine Receptor Antagonist and Beta-2 Adrenoceptor Agonist (MABA) Dual Pharmacology Molecules," Respiratoy Drug Delivery Europe, pp. 47-58 (2013).
McNamara, A., et al., Preclinical Efficacy of THRX-200495, a Dual Pharmacology Muscarinic Receptor Antagonist and β2-Adrenoceptor Agonist (MABA), Pulmonary Pharmacology & Therapeutics, xxx pp. 1-7 (2012). Article in press.
Norman, P., "Evaluation of WO-2012085582 and WO-2012085583 two identified MABAs: backups to AZD-2115?" Expert Opin. Ther. Patents, 22(11), pp. 1377-1383 (2012).
Norman, P., "Novel dihydroquinoline-based MABAs; clues to the identity of LAS-190792: evaluation of WO20111411802," Expert Opin. Ther. Patents, 22.2, pp. 185-192 (2012).
Norris, V. et al., "Bronchodilation and Safety of Supratherapeutic Doses of Salbutamol or Ipratropium Bromide Added to Single Dose GSK961081 in Patients with Moderate to Severe COPD," Pulmonary Pharmacology and Therapeutics, vol. 26, pp. 574-580 (2013).
Welders, Pascal L.M.L. et. al., "A New Class of Bronchodilator Improves Lung Function in COPD: a trial with GSK961081" Eur Respir J. 42: pp. 972-981 (2013).
Chung. K.F., "p38 Mitogen-Activated Protein Kinase Pathways in Asthma and COPD," Chest, 139(6): pp. 1470-1479 (2011).
Miller-Larsson, A., "Advances in Asthma and COPD Treatment: Combination Therapy with Inhaled Corticosteroids and Long-Acting β2 Agonists," Curr Pharm Des. 12(25): pp. 3261-3279 (2006).
Ray, Nicholas C. et al., "Muscarinic Antagonist-β-Adrenergic Agonist Dual Pharmacology Molecules as Bronchodilators: a Patent Review," Informa Healthcare, vol. 19, No. 1, pp. 1-12 (2009).
Rogers, D.F.,"Tachykinin Receptor Antagonists for Asthma and COPD," Exert Opin Ther Patents, 11(7): pp. 1097-1121 (2001).
Shan, W. et al., "Dual β2-adrenoceptor Agonists-PDE4 Inhibitors for the Treatment of Asthma and COPD," Bioorg Med Chem Lett, 22: pp. 1523-1526 (2012).
Thorsson, L., "Factors guiding the choice of delivery devices for inhaled corticosteroids in the long-term management of stable asthma and COPD: Focus on budesonide," Respir Med, 99: pp. 836-849 (2005).
Restriction Requirement dated Feb. 20, 2015, in U.S. Appl. No. 13/697,060.
Restriction Requirement dated Feb. 18, 2015, in U.S. Appl. No. 14/357,400.
Office Action dated Feb. 3, 2015, U.S. Appl. No. 14/357,344.
Office Action dated Jun. 2, 2015, U.S. Appl. No. 14/357,344.
Notice of Allowance dated Sep. 2, 2015, in U.S. Appl. No. 14/357,344.
Bastin, R.J. et al., "Salt Selection and Optimisation for Pharmaceutical New Chemical Entities," Organic Process Research and Development, vol. 4, No. 5, pp. 427-435 (2000).
Rahul, Banerjee et al., "Synthon Robustness in Saccarinate Salts of Some Substituted Pyridines," CrystEngComm, vol. 8, No. 9, p. 680-685 (2006).
International Search Report of International Application No. PCT/EP2014/053871, Mar. 27, 2014.
U.S. Appl. No. 14/906,957, filed Jan. 22, 2016.
U.S. Appl. No. 14/906,991, filed Jan. 22, 2016.

(56) References Cited

OTHER PUBLICATIONS

U.S. Appl. No. 15/068,926, filed Mar. 14, 2016.
Requirement for Restriction/Election dated Feb. 11, 2016, for U.S. Appl. No. 14/770,200.
Requirement for Restriction/Election dated Mar. 21, 2016, for U.S. Appl. No. 14/956,767.
Notice of Allowance dated Dec. 15, 2015, in U.S. Appl. No. 13/697,060.
Non-Final Office Action dated Aug. 4, 2015, for U.S. Appl. No. 13/697,060.
Non-Final Office Action dated Mar. 8, 2016, for U.S. Appl. No. 14/956,836.
Non-Final Office Action dated Mar. 21, 2016, for U.S. Appl. No. 14/653,048.
Non -Final Office Action dated Jun. 10, 2016, for U.S. Appl. No. 14/770,200.
Non-Final Office Action dated Jul. 8, 2016, for U.S. Appl. No. 14/956,767.
Non-Final Office Action dated Jul. 11, 2016, for U.S. Appl. No. 15/068,926.
Berge, S. et al., Pharmaceut. Sc., 1977, vol. 66(1), pp. 1-19.

* cited by examiner

FTIR spectrum for *trans*-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)cyclohexyl hydroxy(di-2-thienyl)acetate.

X-ray diffraction (PXRD) pattern for trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)-(methyl)amino)cyclohexyl hydroxy(di-2-thienyl)acetate ethanedisulfonate..

¹H-NMR (600 MHz, DMSO-d6) for trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)cyclohexyl hydroxy(di-2-thienyl)acetate ethanedisulfonate.

DSC analysis of *trans*-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)-amino)cyclohexyl hydroxy(di-2-thienyl)acetate ethanedisulfonate.

TGA analysis of trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)-amino)cyclohexyl hydroxy(di-2-thienyl)acetate ethanedisulfonate FTIR spectrum for trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)cyclohexyl hydroxy(di-2-thienyl)acetate ethanedisulfonate FTIR spectrum for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)(methyl)-amino)cyclohexyl 2-hydroxy-2,2-di(thiophen-2-yl)acetate.

X-ray diffraction (PXRD) pattern for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate.

$^1$H-NMR spectrum of *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate.

DSC analysis of *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate TG analysis for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate.

FTIR spectrum for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy)ethyl)(methyl)-amino)cyclohexyl 2-hydroxy-2,2-di(thiophen-2-yl)acetate disaccharinate X-ray diffraction (PXRD) pattern for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate L-tartrate.

$^1$H-NMR spectrum of *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate L-tartrate.

DSC analysis of *trans*-4-((2-(2-chloro-4-(((R)-2-hydroxy-2-(8-hydroxy-2-oxo-1,2-dihydro-quinolin-5-yl)ethylamino)methyl)-5-methoxyphenylcarbamoyloxy)ethyl)-(methyl)amino)-cyclohexyl 2-hydroxy-2,2-di(thiophen-2-yl)acetate L-tartrate TG analysis for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate L-tartrate.

FTIR spectrum for *trans*-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy)ethyl)(methyl)-amino)cyclohexyl 2-hydroxy-2,2-di(thiophen-2-yl)acetate L-tartrate

SALTS OF 2-AMINO-1-HYDROXYETHYL-8-HYDROXYQUINOLIN-2(1H)-ONE DERIVATIVES HAVING BOTH β2 ADRENERGIC RECEPTOR AGONIST AND M3 MUSCARINIC RECEPTOR ANTAGONIST ACTIVITIES

This application is a national stage filing under 35 U.S.C. §371 of International Application No. PCT/EP2014/053871, filed on Feb. 27, 2014, which claims priority of European Patent Application No. 13382060.5, filed on Feb. 27, 2013, and also claims priority of U.S. Provisional Patent Application No. 61/804,558 filed on Mar. 22, 2013, The contents of these applications are each incorporated herein by reference.

FIELD OF THE INVENTION

The present invention is directed to pharmaceutically acceptable crystalline addition salts of (i) 2-amino-1-hydroxyethyl-8-hydroxyquinolin-2(1H)-one derivatives and (ii) a hydroxycarboxylic acid, a sulfonic acid or a sulfimide derivative, or a pharmaceutically acceptable solvate thereof. The invention is also directed to pharmaceutical compositions comprising the salts, methods of using them to treat respiratory diseases associated with dual β2 adrenergic receptor agonist and M3 muscarinic receptor antagonist activities, and processes and intermediates useful for preparing such salts.

BACKGROUND OF THE INVENTION

WO 2011/141180 A1 discloses compounds which are known to have a dual β2 adrenergic receptor agonist and M3 muscarinic receptor antagonist activity. However, many of these compounds cannot be formulated for effective delivery by inhalation as a dry powder. Delivery by inhalation as a dry powder is challenging. It requires careful control of the particle size of the powder which is to be inhaled, and careful control of the particle size distribution. Further, it is important to avoid particle agglomeration or aggregation. In addition, when preparing pharmaceutical compositions and formulations for use in such devices, it is highly desirable to have a crystalline form of a therapeutic agent that is neither hygroscopic nor deliquescent and which has a relatively high melting point (i.e. greater than about 150° C.) thereby allowing the material to be micronized without significant decomposition or loss of crystallinity.

Although the 2-amino-1-hydroxyethyl-8-hydroxyquinolin-2(1H)-one derivatives disclosed in WO 2011/141180 A1 have shown adequate pharmacological behaviour, it has proved difficult to obtain them in the form of a salt which is crystalline, not hygroscopic nor deliquescent and which has a relatively high melting point to enable micronization.

So far no crystalline salt of any of the compounds disclosed in WO 2011/141180 having the desired properties has been reported.

Accordingly, a need exists for stable, non-deliquescent salt forms of at least some of these compounds having acceptable levels of hygroscopicity and relatively high melting points.

SUMMARY OF THE INVENTION

The present invention provides pharmaceutically acceptable crystalline addition salts of (i) 2-amino-1-hydroxyethyl-8-hydroxyquinolin-2(1H)-one derivatives and (ii) a hydroxycarboxylic acid, a sulfonic acid or a sulfimide derivative, or a pharmaceutically acceptable solvate thereof, wherein the 2-amino-1-hydroxyethyl-8-hydroxyquinolin-2(1H)-one derivatives having the following formula (I):

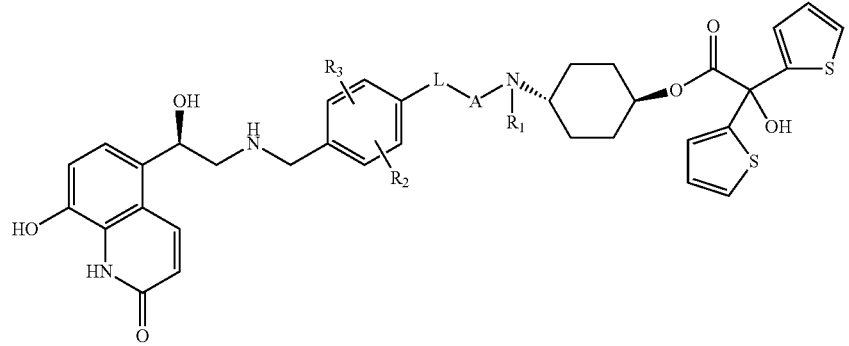

Wherein:
  $R_1$ represents a hydrogen atom or a $C_{1-4}$ alkyl group,
  $R_2$ and $R_3$ independently represent a hydrogen atom, a halogen atom, a $C_{1-4}$ alkyl group, a $C_{1-4}$ alkoxy group and a cyano group,
  A represents a $C_{1-4}$ alkylene group optionally substituted with one or more $C_{1-2}$ alkyl groups,
  L represents a direct bond, —NH(CO)—, —(CO)NH— or —NH(CO)O— group, wherein in the case of —NH(CO)O—, the nitrogen atom is bound to the phenylene substituent and the oxygen atom is bound to the A substituent.
and pharmaceutically acceptable solvates thereof.

The invention also provides a pharmaceutical composition comprising a therapeutically effective amount of a salt of the invention and a pharmaceutically acceptable carrier.

The invention further provides a combination comprising a salt of the invention and one or more other therapeutic agents.

The invention also provides a salt of the invention, a pharmaceutical composition of the invention or a combination of the invention, for use in the treatment of a pathological condition or disease associated with both β2 adrenergic receptor agonist and M3 muscarinic receptor antagonist activity.

The invention further provides the use of a salt of the invention, a pharmaceutical composition of the invention or a combination of the invention, in the manufacture of a medicament for the treatment of a pathological condition or disease associated with both β2 adrenergic receptor agonist and M3 muscarinic receptor antagonist activity.

The invention also provides a method for treating a subject afflicted with a pathological condition or disease associated with both β2 adrenergic receptor agonist and M3 muscarinic receptor antagonist activity, which comprises administering to said subject an effective amount of a salt of the invention, a pharmaceutical composition of the invention or a combination of the invention.

DETAILED DESCRIPTION OF THE INVENTION

Figure 1:
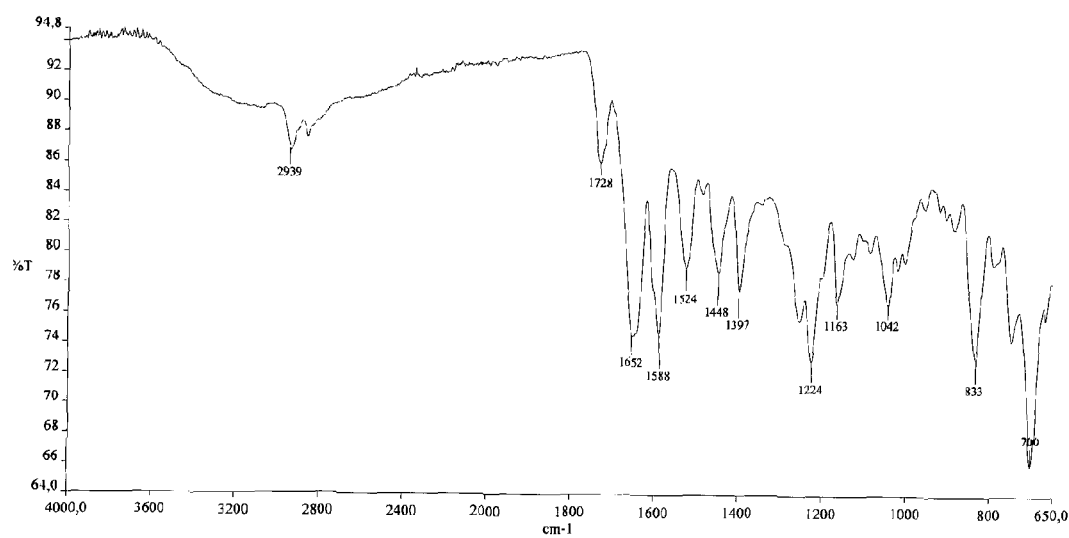
FIG. 1 shows the Fourier Transform Infrared (FTIR) spectrum for trans-4-((3-(2-chloro-4-(((2R)-2-hydroxy-2-(8-hydroxy-2-oxo-1,2-dihydroquinolin-5-yl)ethylamino) methyl)-5-methoxyphenylamino)-3-oxopropyl)(methyl) amino)cyclohexyl hydroxy(di-2-thienyl)acetate.

When describing the salts, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a human patient which includes:
  (a) preventing the disease or medical condition from occurring, i.e., prophylactic treatment of a patient;
  (b) ameliorating the disease or medical condition, i.e., causing regression of the disease or medical condition in a patient;
  (c) suppressing the disease or medical condition, i.e., slowing the development of the disease or medical condition in a patient; or
  (d) alleviating the symptoms of the disease or medical condition in a patient.

The phrase "disease or condition associated with β2 adrenergic receptor agonist and M3 muscarinic receptor antagonist activities" includes all disease states and/or conditions that are acknowledged now, or that are found in the future, to be associated with both β2 adrenergic receptor agonist and M3 muscarinic receptor antagonist activity. Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

On the other hand M3 receptor activity is associated with gastrointestinal-tract disorders such as Irritable bowel syndrome (IBS) (see, for ex., U.S. Pat. No. 5,397,800), GI ulcers, spastic colitis (see, for ex., U.S. Pat. No. 4,556,653); urinary-tract disorders such as urinary incontinence (see, for ex., J. Med. Chem., 2005, 48, 6597-6606), pollakiuria; motion sickness and vagally induced sinus bradycardia.

The term "solvate" refers to a complex or aggregate formed by one or more molecules of a solute, i.e. a salt of the invention or a pharmaceutically-acceptable salt thereof, and one or more molecules of a solvent. Such solvates are typically crystalline solids having a substantially fixed molar ratio of solute and solvent. Representative solvents include by way of example, water, ethanol, isopropanol and the like. The preferred solvate is a hydrate.

As used herein the term $C_{1-4}$ alkyl embraces linear or branched radicals having 1 to 4 carbon atoms. Examples include methyl, ethyl, n-propyl, i-propyl, n-butyl, sec-butyl or t-butyl.

As used herein, the term $C_{1-4}$ alkylene embraces divalent alkyl moieties typically having from 1 to 4 carbon atoms. Examples of $C_{1-4}$ alkylene radicals include methylene, ethylene, propylene and butylene radicals.

As used herein, the term $C_{1-4}$ alkoxy (or alkyloxy) embraces optionally substituted, linear or branched oxy-containing radicals each having alkyl portions of 1 to 4 carbon atoms. Examples of $C_{1-4}$ alkoxy radicals include methoxy, ethoxy, n-propoxy, i-propoxy, n-butoxy, sec-butoxy and t-butoxy.

As used herein, the term halogen atom embraces chlorine, fluorine, bromine or iodine atoms typically a fluorine, chlorine or bromine atom. The term halo when used as a prefix has the same meaning.

Typically, in the compound of formula (I), $R^1$ represents a hydrogen atom or a methyl group, preferably a methyl group.

Typically, in the compound of formula (I), $R^2$ and $R^3$ independently represent a halogen atom or a $C_{1-4}$ alkoxy group, preferably a $C_{1-2}$ alkoxy group. More preferably $R^2$ and $R^3$ independently represents a chlorine atom or a methoxy group, being most preferably $R^2$ represents a methoxy group and $R^3$ represents a chlorine atom.

Typically, in the compound of formula (I), A represents a $C_{1-2}$ alkylene group optionally substituted with one or two methyl group, preferably A represent an ethylene group optionally substituted with a methyl group, being most preferably a non-substituted ethylene group.

Typically, in the compound of formula (I), L represents a —NH(CO)—, —(CO)NH— or —NH(CO)O— group, more preferably L represents a —NH(CO)— or —NH(CO)O— group.

Preferably, in the compound of formula (I), $R^1$ represents a methyl group, $R^2$ represents a methoxy group, $R^3$ represents a chlorine atom, A represent an ethylene group and L represents a —NH(CO)— or —NH(CO)O— group.

Typically, the hydroxycarboxylic acid is selected from the group consisting of citric acid, lactic acid, mucic acid, tartaric acid, pantothenic acid, glucuronic acid, lactobionic acid, gluconic acid, 1-hydroxy-2-naphthoic acid, mandelic and malic acid.

Typically, the sulfonic acid is selected from the group consisting of methanesulfonic acid, ethanedisulfonic acid, benzenesulphonic acid, p-toluenesulfonic acid, naphthalene-1,5-disulfonic acid, napthalene-2-sulfonic acid and (1S)-camphor-10-sulfonic acid.

Typically, the sulfimide derivative is selected from the group consisting of benzoic sulfimide (also known as saccharin), thieno[2,3-d]isothiazol-3(2H)-one 1,1-dioxide and isothiazol-3(2H)-one 1,1-dioxide.

Particular individual salt compounds of the invention include:

trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexyl hydroxy(di-2-thienyl)acetate ethanedisulfonate, trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyloxy)ethyl)-(methyl)amino)-cyclohexyl 2-hydroxy-2,2-di(thiophen-2-yl)acetate disaccharinate, and L-tartrate salt of trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyloxy)ethyl)-(methyl) amino)cyclohexyl 2-hydroxy-2,2-di(thiophen-2-yl) acetate, General Synthetic Procedures The salts of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Processes for preparing salts of the invention are provided as further embodiments of the invention and are illustrated by the procedures below.

The salts of the invention can be synthesized from compounds of formula (I) and from the appropriate hydroxycarboxylic acid, sulfonic acid or sulfimide derivatives, which will generally be commercially available from, for example, Aldrich.

Suitable solvents for carrying out the reaction can be selected by a skilled chemist and may depend on the specific salt to be formed. Mixtures of appropriate solvents may be used, optionally containing water. For example, the appropriate solvents may be selected from methanol, ethanol, dichloromethane, tetrahydrofuran, water or a mixture thereof.

Upon completion of any of the foregoing reactions, the salt can be isolated from the reaction mixture by any conventional means such as precipitation, concentration, centrifugation and the like.

It will be appreciated that while specific process conditions (i.e. reaction temperatures, times, mole ratios of reactants, solvents, pressures, etc.) are given, other process conditions can also be used unless otherwise stated.

To prepare the salts of the present invention, the free base is typically dissolved in an appropriate solvent which in some examples is heated to approximately 60-80° C. Then a solution of the appropriate hydroxycarboxylic acid or sulfonic acid or a sulfimide in an suitable solvent, preferably the same solvent as that in which the free base is dissolved, is typically added to the heated solution. The mixture is then optionally stirred for 15-300 minutes at 60-80° C. or at room temperature. The mixture is then typically cooled, for example down to 20-25° C. or 0-5° C. The precipitate formed is isolated by filtration, washed with an appropriate solvent and dried for example in vacuum.

Pharmaceutical Compositions

The invention also encompasses pharmaceutical compositions comprising a therapeutically effective amount of a salt of the invention or an enantiomer or pharmaceutically acceptable solvate thereof and a pharmaceutically acceptable carrier. Typically the pharmaceutical composition is formulated for administration by inhalation, preferably as a dry powder.

Typically, the pharmaceutical composition further comprises a therapeutically effective amount of one or more other therapeutic agents.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Dry powder compositions for topical delivery to the lung by inhalation may, for example, be presented in capsules and cartridges of for example gelatine or blisters of for example laminated aluminium foil, for use in an inhaler or insufflator. Formulations generally comprise a powder mix for inhalation of the salt of the invention and a suitable powder base (carrier substance) such as lactose or starch. Use of lactose is preferred. The powder base may include additional components such as preservatives, stabilizing agents, absorption enhancers or aerodynamic modifier.

Each capsule or cartridge may generally contain between 0.1 μg and 9000 μg of each therapeutically active ingredient. Alternatively, the active ingredient (s) may be presented without excipients.

Packaging of the formulation may be suitable for unit dose or multi-dose delivery. In the case of multi-dose delivery, the formulation can be pre-metered or metered in use. Dry powder inhalers are thus classified into three groups: (a) single dose, (b) multiple unit dose and (c) multi dose devices.

For inhalers of the first type, single doses have been weighed by the manufacturer into small containers, which are mostly cartridges or hard gelatine capsules. In the case of a cartridge, the single-dose inhaler is thus composed of a cartridge containing the inhalation powder and metering the individual dosages. The powder for inhalation is permanently situated in the bottom of cartridge, in a reservoir with a metering slide at the base and a lid at the top. When a capsule is used as a container, the capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients.

Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen et al, 1997).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g. WO91/02558 and GB 2242134). They comprise the type of multiple unit dose inhalers together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring plungers with a local or circumferential recess to displace a certain volume of powder from the container to a delivery chamber or an air conduit (e.g. EP 0505321, WO 92/04068 and WO 92/04928), or measuring slides such as the Genuair® devise (formerly known as Novolizer SD2FL) which is described in the following patent applications: WO 97/000703, WO 03/000325 and WO2006/008027

Additional Therapeutic Agents

The salts of the present invention can also be used in combination with other drugs known to be effective in the treatment of the diseases or the disorders indicated above. For example the salts of the present invention can be combined with (a) corticosteroids, or gluococorticoids (b) antihistamines (c) chemokine receptor antagonists, such as maraviroc or enfuvirtide, (e) CRth2 antagonists, (f) leukotriene receptor antagonists, (g) JAK inhibitors such as tofacitinib or INCB018424, (h) Syk inhibitors (i) phosdiesterase IV inhibitors (j) p38 Inhibitors such as ARRY-797, (k) PKC inhibitors such as NVP-AEB071, (l) 5-lipoxygenase activating protein inhibitors, such as veliflapon, (m) 5-lipoxygenase inhibitors, (n) CYSLTR1 antagonists (o) CYSLTR2 antagonists (p) BLT1 antagonists, (q) BLT2 antagonists, (r) thromboxane A2 antagonists such as ramatroban, (s) DP1 receptor antagonists, such as laropiprant, (t) DP1 receptor agonists, such as BW-245C, (u) IP receptor agonists, such as RO-1138452, (v) Anti-IgE, such as omalizumab, (w) IL5 antibody, such as mepolizumab, (x) leukotriene formation inhibitors, (y) decongestants, such as ephedrine, levo-methamphetamine, naphazoline, oxymetazoline, phenylephrine, phenylpropanolamine, propylhexedrine, pseudoephedrine, synephrine or tetrahydrozoline; (z) mucolytics such as acetylcysteine, ambroxol, bromhexine, carbocisteine, domiodol, eprazinone, erdosteine, letosteine, neltenexine, sobrerol, stepronin or tiopronin; (aa) antitussives, such as dextromethorphan, (bb) analgesics such as aspirin, paracetamol, rofecoxid, celecoxib, morphine, codeine, oxycodone, hydrocodone, dihydromorphine or flupirtine; and (cc) expectorants such antimony pentasulfide, guaiacolsulfonate, guaifenesin, potassium iodide or tyloxapol.

Accordingly, another embodiment of the invention is a combination product comprising (i) at least a salt compound as defined previously, and (ii) one or more active ingredients as described above, for simultaneous, separate or sequential use in the treatment of the human or animal body.

A preferred embodiment of the invention is a combination product as defined before for the treatment or prevention of pathological conditions, diseases and disorders associated with both β2 adrenergic receptor and M3 antimuscarinic activity, in particular wherein the pathological condition or disease is selected from asthma, acute or chronic bronchitis, emphysema, or Chronic Obstructive Pulmonary Disease (COPD), preferably asthma and COPD, as well as a method for treating a subject afflicted with a pathological condition or disease associated with both β2 adrenergic receptor and M3 antimuscarinic activity, in particular wherein the pathological condition or disease is as described above; which comprises administering to said subject an effective amount of a combination product as defined before.

As indicated above, the salts according to the invention may also be used in combination with another therapeutically active agent as defined above.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

Examples of suitable PDE4 inhibitors that can be combined with salt compounds of the present invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid (MK-0873), CDC-801, UK-500001, BLX-914, 2-carbomethoxy-4-cyano-4-(3-cyclopropylmethoxy-4-difluromethoxyphenyl)cyclohexan1-one, cis[4-cyano-4-(3-cyclopropylmethoxy-4-difluoromethoxyphenyl)cyclohexan-1-ol, CDC-801 and 5(S)-[3-(Cyclopentyloxy)-4-methoxyphenyl]-3(S)-(3-methylbenzyl)piperidin-2-one (IPL-455903).

Examples of suitable corticosteroids and glucocorticoids that can be combined with salt compound of the present invention are prednisolone, methylprednisolone, dexamethasone, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone, mometasone furoate, rimexolone, prednisolone farnesylate, ciclesonide, butixocort propionate, RPR-106541, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, Desisobutyrylciclesonide, hydrocortisone acetate, hydrocortisone sodium succinate, NS-126, prednisolone sodium phosphate and hydrocortisone probutate, Prednisolone sodium metasulfobenzoate and clobetasol propionate.

Examples of suitable anti-histamines that can be combined with the salts of the invention are methapyrilene, mequitazine, azelastine hydrochloride, acrivastine, emedastine difumarate, emedastine fumarate, loratadine, cyproheptadine hydrochloride, diphenhydramine hydrochloride, doxepin hydrochloride, promethazine hydrochloride, levocabastine hydrochloride, desloratadine, cinnarizine, setastine hydrochloride, mizolastine, ebastine, cetirizine hydrochloride, epinastine hydrochloride, olopatadine hydrochloride, bepotastine besilate, triprolidine hydrochloride, rupatadine fumarate, fexofenadine hydrochloride, levocetirizine dihydrochloride, ketotifen, azatadine maleate, dimethindene maleate, clemastine fumarate, alcaftadine, bilastine, vapitadine hydrochloride, AZD-1744, GSK-1004723D, GSK-835726 or SUN-1334H.

Examples of suitable leukotriene antagonist that can be combined with the salts of the present invention are CYS-LTR1 antagonists, such as montelukast, pranlukast or zafirlukast; or CYSLTR2 antagonists, such as pranlukast, zafirlukast or tipilukast.

Examples of suitable CRTH$_2$ antagonist that can be combined with the salts of the present invention are ramatroban, AMG-009, OC-000459).

Examples of suitable Syk kinase inhibitors that can be combined with the salts of the present invention are fosfamatinib (from Rigel), R-348 (from Rigel), R-343 (from Rigel), R-112 (from Rigel), piceatannol, 2-(2-Aminoethylamino)-4-[3-(trifluoromethyl)phenylamino]pyrimidine-5-carboxamide, R-091 (from Rigel), 6-[5-Fluoro-2-(3,4,5-trimethoxyphenylamino)pyrimidin-4-ylamino]-2,2-dimethyl-3,4-dihydro-2H-pyrido[3,2-b][1,4]oxazin-3-one benzenesulfonate (R-406 from Rigel), 1-(2,4,6-Trihydroxyphenyl)-2-(4-methoxyphenyl)ethan-1-one, N-[4-[6-(Cyclobutylamino)-9H-purin-2-ylamino]phenyl]-N-methylacetamide (QAB-205 from Novartis), CI-1002 (from Pfizer), VRT-750018 (from Vertex), PRT-062607, 2-[7-(3,4-Dimethoxyphenyl)imidazo[1,2-c]pyrimidin-5-ylamino]pyridine-3-carboxamide dihydrochloride (BAY-61-3606 from Bayer) and AVE-0950 (from Sanofi-Aventis).

Treatment of a Pathological Conditions or Diseases Associated with Both β2 Adrenergic Receptor and M3 Antimuscarinic Activity The salts of the invention, pharmaceutical compositions and the combinations of the invention may be used in the treatment of pathological conditions or diseases associated with both β2 adrenergic receptor and M3 antimuscarinic activity, typically respiratory diseases. The respiratory disease is preferably one in which the use of bronchodilating agents is expected to have a beneficial effect, for example asthma, acute or chronic bronchitis, emphysema, or Chronic Obstructive Pulmonary Disease (COPD). Asthma or chronic obstructive pulmonary disease are more preferred.

The active compounds in the combination and the second therapeutic agent as defined above, may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

The active compound(s) formulations generally contain a suitable carrier which may be either a propellant for MDI administration or water for administration through a nebuliser. The formulation may comprise additional components such as preservatives (for example, benzalkonium chloride, potassium sorbate, benzyl alcohol); pH stabilizers (for example, acidic agents, alkaline agents, buffer systems); isotonic stabilizers (for example, sodium chloride); surfactant and wetting agents (for example, polysorbates, sorbitan esters); and/or absorption enhancers (for example, chitosan, hyaluronic acid, surfactants). The formulation may also contain additives to improve the solubility of other active compounds when mixed with the salt of the invention. The solubility enhancers may comprise components such as cyclodextrins, liposomes or co-solvents such as ethanol, glycerol and propylene glycol.

Additional suitable carriers for formulations of the active salts of the present invention can be found in Remington: The Science and Practice of Pharmacy, 20th Edition, Lippincott Williams & Wilkins, Philadelphia, Pa., 2000.

The carrier for a pharmaceutical composition in the form of a dry powder is typically chosen from starch or a pharmaceutically acceptable sugar, such as lactose or glucose. The amount of the active ingredient to the carrier will generally vary from 0.001% to 99%.

The invention further encompasses a method of treating diseases or conditions associated with both β2 adrenergic receptor and M3 antimuscarinic activity, typically respiratory diseases, such as asthma or chronic obstructive pulmonary disease, in a mammal, the method comprising administering to the mammal, a therapeutically effective amount of a salt, pharmaceutical composition or combination of the invention. The mammal is preferably a human being.

EXAMPLES

Reagents, starting materials, and solvents were purchased from commercial suppliers and used as received.

Crystallizations test of salts of compounds of formula (I) with a broad range of pharmaceutically acceptable acids (comprising among others fumaric, succinic, sulphuric, 1-hydroxy-2-naphthoic, L-tartaric, hydrobromic, 4-acetamidobenzoic, sorbic, hydrochloric, oxalic, triphenylacetic, methanesulfonic, ethanedisulfonic, p-toluenesulfonic, naphthalene-2-sulfonic, saccharin, L-mandelic, maleic, 1S-camphor-10-sulfonic, L-malic, L-pyroglutamic and naphthalene-1,5-disulfonic acids) in a range of different pharmaceutically acceptable solvents (including among others acetone, ethyl acetate, isopropanol, 2-butanol, ethanol, chloroform, methanol, tetrahydrofurane and water or mixtures thereof) have been undertaken.

The salts from 4-acetamidobenzoic acid and sorbic acid rendered either oils or amorphous solids. The salt from sulphuric acid, was obtained as solid but with a very low crystallinity. On the other hand, the salts from hydrochloric acid and hydrobromic acid were instable.

Only the salts of the invention were very crystalline. In addition this crystalline salts were neither hygroscopic nor deliquescent and had a relatively high melting point allowing them to be micronized and to have long term stability.

Particularly good methods to prepare the addition salts of the invention are illustrated in the following examples.

The FTIR spectra were recorded using either a Bruker Alpha spectrometer, equipped with a Bruker Diamond single reflection ATR system, a mid-infrared source as the excitation source and a DTGS detector, or using a Perking Elmer, Spectrum one spectrometer, equipped with a Diamond single reflection ATR system, a mid-infrared source as the excitation source and a DTGS detector. The spectra were acquired in 32 scans at a resolution of 4 cm-1 in the range of 4000-400 $cm^{-1}$.

DSC analyses were recorded either in a Mettler Toledo DSC822e or using a DSC-821 Mettler-Toledo, serial number 5117423874. In the case of a Mettler Toledo DSC822e equipment, samples of 1-3 mg were weighted (using a microscale MX5, Mettler) into 40 μL aluminium crucibles with a pinhole lid, and were heated, under nitrogen flow (50 mL/min), from 30 to 300° C. at a heating rate of 10° C./min. Data collection and evaluation was done with software STARe. In case of a DSC-821 Mettler-Toledo, serial number 5117423874 equipment, samples were weighed into an aluminium pan, an aluminium pinhole lid placed on top of the sample and compressed with a brass rod. Samples were equilibrated at 25° C. and heated at 10° C./min to 300° C. The instrument was calibrated using indium and zinc standards.

Thermogravimetric analyses were recorded in a Mettler Toledo SDTA851e. Samples of 1-3 mg were weighted (using a microscale MX5, Mettler) 40 μL aluminium crucibles with a pinhole lid, and were heated at 10° C./min between 30 and 300° C., under nitrogen flow (50 mL/min). Data collection and evaluation was done with software STARe.

Proton nuclear magnetic resonance analyses were recorded in deuterated dimethylsulfoxide (DMSO-d6) in a Bruker Avance 500 Ultrashield NMR spectrometer and a Varian VNMRS 600 MHz with coldprobe. Spectra were acquired solving 8-10 mg of sample in 0.5 mL of deuterated solvent.

In order to acquire a powder diffraction pattern of the obtained solid, approximately 20 mg of the non-manipulated samples were prepared in standard sample holders using foils of polyacetate.

Powder diffraction patterns were acquired on a Bruker D8 Advance Series 2Theta/Theta powder diffraction system using CuKα1-radiation (1.54060 A) in transmission geometry. The system is equipped with a VĂNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0.

Powder diffraction patterns were also performed on a Brucker X-ray powder diffractometer, model D2 Phaser with a Cu X-ray source. The method runs from 5 to 40 degrees 2-Theta with a 0.01 degree 2-Theta step size and a 0.4 second collection time at each step using a Lynxeye detector.

Example 1

Preparation of trans-4-((3-(2-chloro-4-M2R)-2-hydroxy-2-(8-hydroxy-2-oxo-1,2-dihydroquinolin-5-Aethylamino)methyl)-5-methoxyphenylamino)-3-oxopropyl)(methyl)amino)-cyclohexyl hydroxy(di-2-thienyl)acetate ethanedisulfonate 1.1 Preparation of free base of trans-4-((3-(2-chloro-4-(((2R)-2-hydroxy-2-(8-hydroxy-2-oxo-1,2-dihydro-quinolin-5-yl)ethylamino)methyl)-5-methoxyphenyl-amino)-3-oxopropyl)(methyl)-amino)cyclohexyl hydroxy(di-2-thienyl)acetate from hydrofluoride salt thereof To a suspension of 1.15 g of trans-4-((3-(2-chloro-4-M2R)-2-hydroxy-2-(8-hydroxy-2-oxo-1,2-dihydroquinolin-5-yl)ethylamino)methyl)-5-methoxyphenylamino)-3-oxopropyl)-(methyl)amino)cyclohexyl hydroxy(di-2-thienyl) acetate hydrofluoride (Example 9 of WO 2011/141180) in 50 ml of $CHCl_3$, excess of saturated $NaHCO_3$ aqueous solution was added. The mixture was stirred during five minutes at room temperature. The solid became an oil and $CHCl_3$/MeOH (10:1) solution was added until dissolution was observed. The phases were separated and the aqueous phase was extracted again with 30 ml of $CHCl_3$/MeOH (10:1) solution. The organic phases were combined, dried under $MgSO_4$, filtered and solvents were concentrated under reduced pressure to obtain 1.09 g of the free base as a yellow dry foam. (Yields: 97.17%).

FIG. 1 shows the FTIR spectrum for trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)cyclohexyl hydroxy(di-2-thienyl)acetate free base. Significant signal for the free base compound appears at: 2939, 1728, 1652, 1588, 1524, 1448, 1397, 1224, 1163, 1042, 833 and 700 $cm^{-1}$.

1.2 Direct preparation of crystalline ethanedisulfonate salt from trans-4-((3-(2-chloro-4-(((2R)-2-hydroxy-2-(8-hydroxy-2-oxo-1,2-dihydroquinolin-5-yl)ethylamino)-methyl)-5-methoxyphenylamino)-3-oxopropyl)(methyl)amino)-cyclohexyl hydroxyl-(di-2-thienyl)acetate free base 1.2.1 Using Methanol as a Solvent 105 mg of the free base (0.132 mmol) were dissolved in 14 ml of methanol under magnetic stirring and using occasional sonication. The solution was filtered through a 0.45 μm syringe filter to eliminate some slight yellow cloudiness and then, maintaining moderate stirring, a solution of 27.6 mg (0.145 mmol) of ethanedisulfonic acid in 1 ml of methanol was added dropwise. A clear solution was obtained after the addition. The formation of a white cloudiness started several minutes later and then the amount of precipitate increased gradually. The stirring was continued for 1 hour and then the mixture was allowed to stand at room temperature 24 hours. The white solid was filtered, washed once with methanol/isopropyl ether (1:1) solution and three times with ethyl ether to give, after drying, 76 mg of the title salt. (Yields: 58.5%).

1.2.2 Using $CH_2Cl_2$/EtOH as a Solvent

Under magnetic stirring 105 mg of the free base (0.132 mmol) were dissolved in 3 ml of dichloromethane and 3 ml of ethanol were added. The solution was filtered through a 0.45 μm syringe filter to eliminate a very slight yellow cloudiness and then, maintaining moderate stirring, a solution of 27.6 mg (0.145 mmol) of ethanedisulfonic acid in 1 ml of ethanol was added dropwise. The formation of a white cloudiness started immediately after the addition of the first drops of the acid solution and then the precipitate increased gradually. The stirring was continued for 1 hour and then the mixture was allowed to stand at room temperature 24 hours. The white solid was filtered, washed once with ethanol/isopropyl ether (3:1) solution and three times with ethyl ether to give, after drying, 99 mg of the title salt. (Yields: 76.1%).

Figure 2:
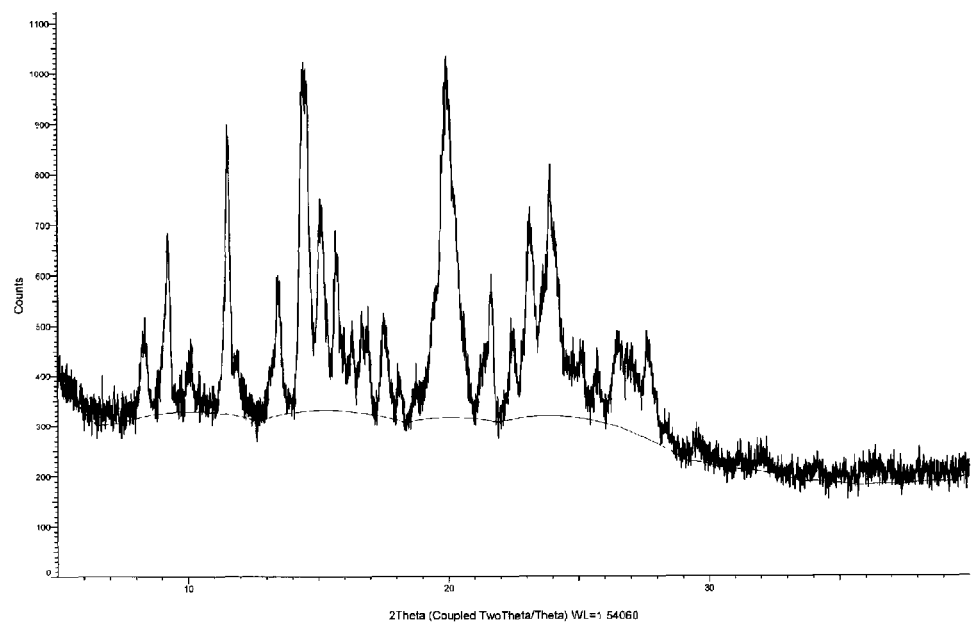
FIG. 2 shows the Powder X-Ray Diffraction (PXRD) pattern for trans-4-((3-(2-chloro-4-(((2R)-2-hydroxy-2-(8-hydroxy-2-oxo-1,2-dihydroquinolin-5-yl)ethylamino) methyl)-5-methoxyphenylamino)-3-oxopropyl)(methyl) amino)cyclohexyl hydroxy(di-2-thienyl)acetate ethanedisulfonate.

FIG. 2 shows the powder X-ray diffraction (PXRD) pattern for the ethanedisulfonate salt. A large number of peaks were observed thus confirming the crystallinity of the salt. The summary of the XRPD angles and relative intensities are given in Table 1.

TABLE 1

| Diffraction Angle (°2θ) | d value (Å) | Relative Intensity (%) |
|---|---|---|
| 9.22 | 9.58 | 49.3 |
| 11.53 | 7.67 | 70.5 |
| 13.46 | 6.57 | 36.3 |
| 14.46 | 6.12 | 87.6 |
| 14.53 | 6.09 | 93.4 |
| 15.10 | 5.86 | 51.3 |
| 15.12 | 5.85 | 54.9 |
| 15.70 | 5.64 | 50.0 |
| 16.30 | 5.43 | 28.6 |
| 16.67 | 5.31 | 30.7 |
| 16.88 | 5.25 | 25.7 |
| 17.51 | 5.06 | 31.6 |
| 19.44 | 4.56 | 37.1 |
| 19.83 | 4.47 | 81.9 |
| 19.95 | 4.45 | 100 |
| 20.22 | 4.39 | 63.8 |
| 21.64 | 4.10 | 38.7 |
| 22.44 | 3.96 | 27.6 |
| 22.50 | 3.95 | 31.8 |
| 22.88 | 3.88 | 27.2 |
| 23.15 | 3.84 | 62.4 |
| 23.73 | 3.75 | 46.3 |

TABLE 1-continued

| Diffraction Angle (°2θ) | d value (Å) | Relative Intensity (%) |
| --- | --- | --- |
| 23.92 | 3.72 | 68.5 |
| 27.66 | 3.22 | 32.1 |
| 27.70 | 3.22 | 29.6 |

As can be seen form Table 1, the ethanedisulfonate salt of trans-4-((3-(2-chloro-4-(((2R)-2-hydroxy-2-(8-hydroxy-2-oxo-1,2-dihydroquinolin-5-yl)ethylamino)-methyl)-5-methoxyphenylamino)-3-oxopropyl)(methyl)amino)-cyclohexyl hydroxyl-(di-2-thienyl)acetate is characterized by an X-ray powder diffraction (XRPD) pattern having a significant peak at 2θ values of 19.95±0.2, preferably significant peaks at 2θ values of 14.53±0.2, 19.83±0.2 and 19.95±0.2.

Figure 3:
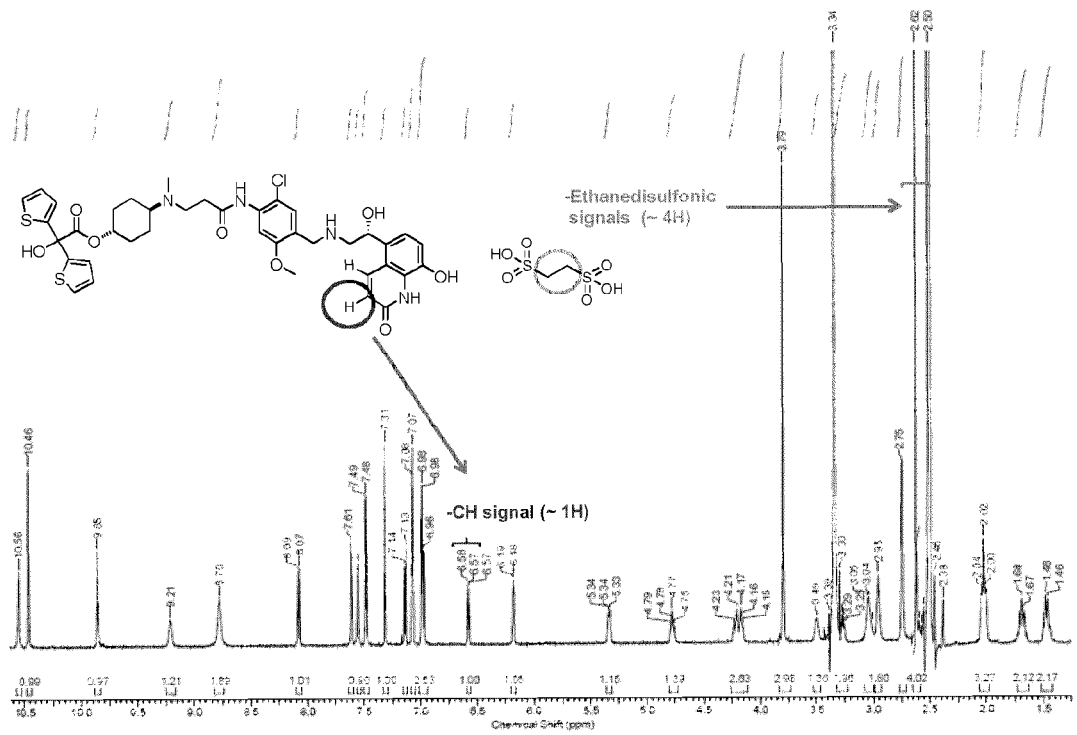
FIG. 3 shows the $^1$H-NMR (600 MHz, DMSO-d6) for trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)cyclohexyl hydroxy(di-2-thienyl)acetate ethanedisulfonate.

FIG. 3 corresponds to the $^1$H-NMR spectrum of the ethanedisulfonate salt. It clearly shows a stoichiometry ratio of 1:1 free base/ethanedisulfonic acid, as inferred from the comparison between the integral values of the protons corresponding to the ethylene group of the acid and that of one single proton of the quinolone moiety of the parent structure.

$^1$H NMR (600 MHz, DMSO-$d_6$) δ ppm 1.42-1.51 (m, 2H), 1.59-1.79 (m, 2H), 1.99-2.07 (m, 4H), 2.61 (s, 4H), 2.74 (d, 3H), 2.93-2.98 (m, 2H), 3.00-3.08 (m, 2H), 3.22-3.33 (m, 2H), 3.46-3.53 (m, 1H), 3.79 (s, 3H), 4.12-4.25 (m, 2H), 4.74-4.81 (m, 1H), 5.31-5.36 (m, 1H), 6.18 (d, 1H), 6.57 (d, J=10.0 Hz, 1H), 6.95-7.00 (m, 3H), 7.07 (d, 2H), 7.14 (d, 1H), 7.31 (s, 1H), 7.48 (d, 2H), 7.55 (s, 1H), 7.61 (s, 1H), 8.08 (d, J=10.0 Hz, 1H), 8.78 (s, 2H), 9.21 (s, 1H), 9.85 (s, 1H), 10.46 (s, 1H), 10.56 (s, 1H).

Figure 4:
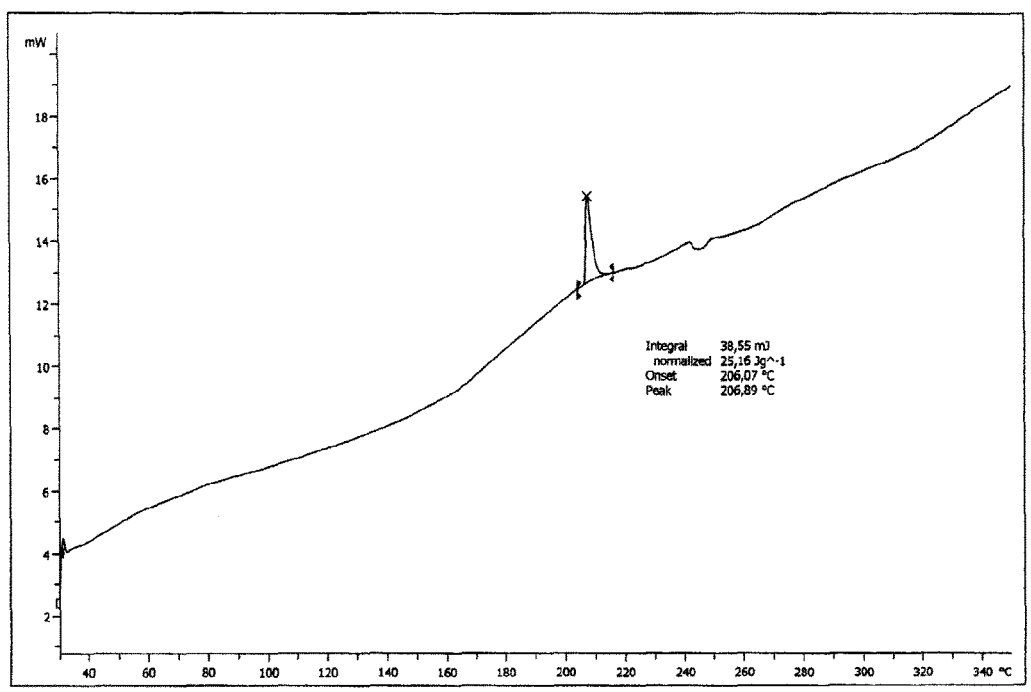
FIG. 4 shows the differential scanning calorimetry (DSC) analysis of trans-4-((3-(2-chloro-4-(((2R)-2-hydroxy-2-(8-hydroxy-2-oxo-1,2-dihydroquinolin-5-yl)ethylamino) methyl)-5-methoxyphenylamino)-3-oxopropyl)(methyl) amino)cyclohexyl hydroxy(di-2-thienyl)acetate ethanedisulfonate.

FIG. 4 shows the DSC analysis for the ethanedisulfonate salt showing only an intense endothermic curve with a maximum at 206° C., indicating a possible fusion/decomposition of the salt.

Figure 5:
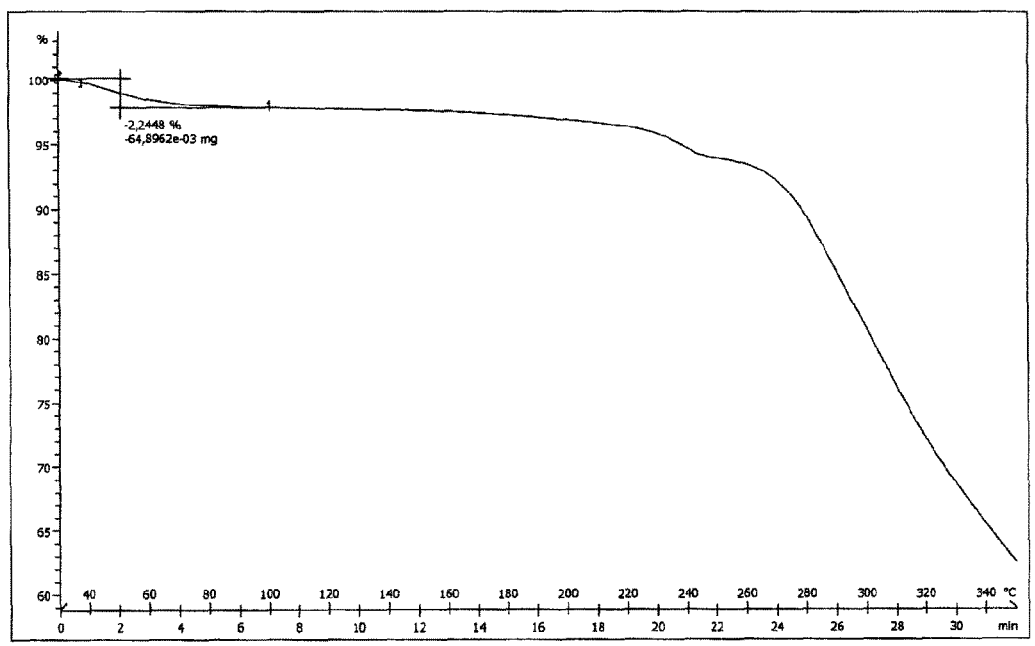
FIG. 5 shows the thermogravimetric (TG) analysis of trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)cyclohexyl hydroxy(di-2-thienyl)acetate ethanedisulfonate.

FIG. 5 shows the TG analysis for the ethanedisulfonate salt. The spectrum shows a slight loss of mass between 40 and 90° C. No significant changes are observed until about 250° C., in which the salt decomposes.

Figure 6:
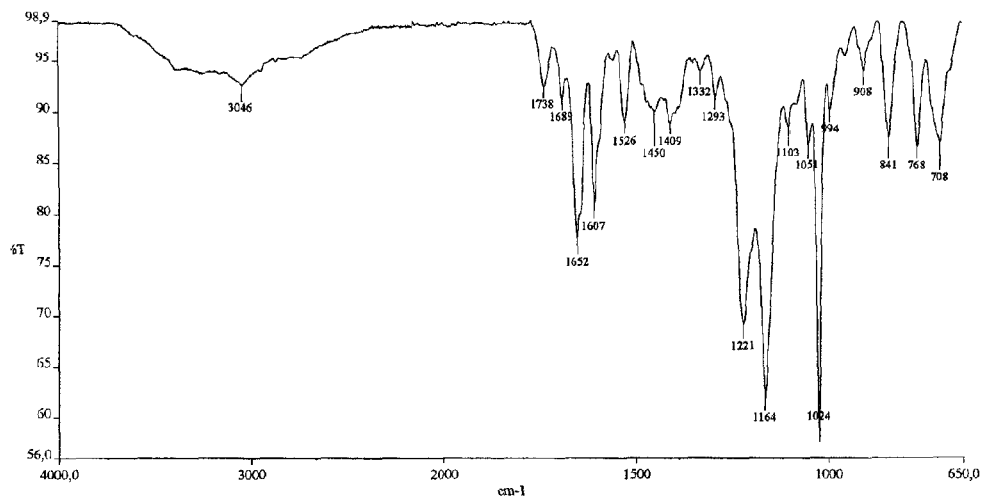
FIG. 6 shows the Fourier transform infrared (FTIR) spectrum for trans-4-((3-(2-chloro-4-(((2R)-2-hydroxy-2-(8-hydroxy-2-oxo-1,2-dihydroquinolin-5-yl)ethylamino) methyl)-5-methoxyphenylamino)-3-oxopropyl)(methyl) amino)cyclohexyl hydroxy(di-2-thienyl)acetate ethanedisulfonate.

FIG. 6 shows the FTIR spectrum for the ethanedisulfonate salt. Significant signal for the ethanedisulfonate salt appears at: 3046, 1738, 1689, 1652, 1607, 1526, 1450, 1409, 1332, 1293, 1221, 1164, 1103, 1051, 1024, 994, 908, 841, 768 and 708 cm$^{-1}$.

Example 2

Preparation of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)-ethyl)(methyl)amino)cyclohexyl 2-hydroxy-2,2-di(thiophen-2-yl)acetate disaccharinate 2.1 Preparation of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)-ethyl)(methyl)amino)cyclohexyl 2-hydroxy-2,2-di(thiophen-2-yl)acetate free base from hydrofluoride To a suspension of 1.26 g of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate hydrofluoride (Example 12 of WO 2011/141180) in 58 ml of CHCl$_3$, excess of saturated NaHCO$_3$ aqueous solution was added. The mixture was stirred during 1 hour at room temperature. The aqueous layer was extracted twice with chloroform. The combined organic phases were dried under Na$_2$SO$_4$, filtered and solvents were concentrated under reduced pressure to obtain 1.2 g of the free base as a yellow dry foam. (Yields: 97.58%)

Figure 7:
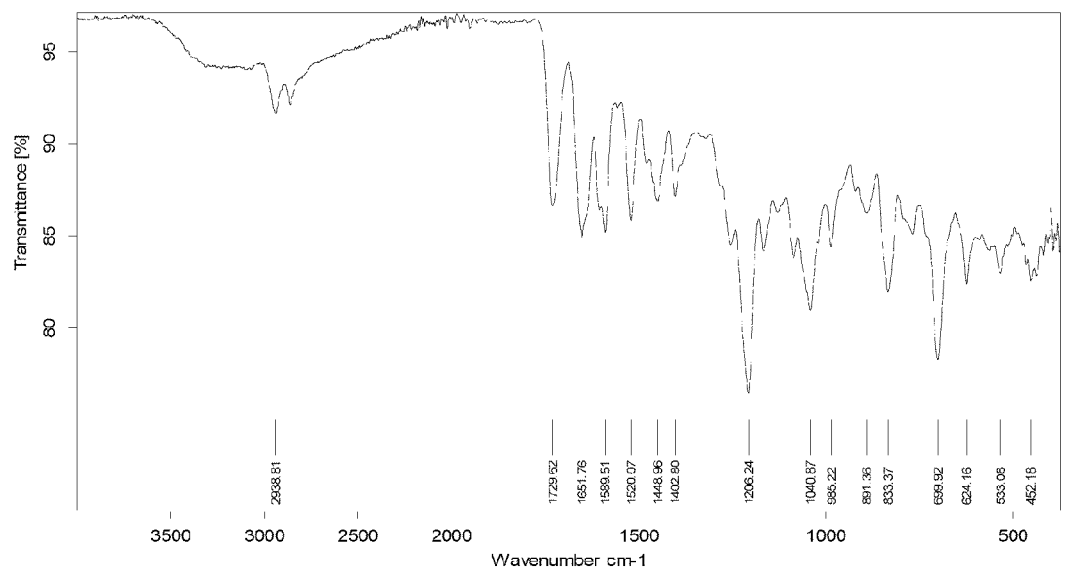
FIG. 7 shows the Fourier transform infrared (FTIR) spectrum for trans-4-((2-(2-chloro-4-(((R)-2-hydroxy-2-(8-hydroxy-2-oxo-1,2-dihydroquinolin-5-yl)ethylamino) methyl)-5-methoxyphenylcarbamoyloxy)ethyl)(methyl) amino)cyclohexyl 2-hydroxy-2,2-di(thiophen-2-yl)acetate.

FIG. 7 shows the Fourier transform infrared (FTIR) spectrum for trans-4-((2-(2-chloro-4-(((R)-2-hydroxy-2-(8-hydroxy-2-oxo-1,2-dihydroquinolin-5-yl)ethylamino) methyl)-5-methoxyphenylcarbamoyloxy)ethyl)(methyl) amino)cyclohexyl 2-hydroxy-2,2-di(thiophen-2-yl)acetate free base. Significant signal for the free base compound appears at: 2939, 1729, 1651, 1589, 1520, 1448, 1402, 1206, 1040, 985, 891, 833, 699, 624, 533 and 452 cm$^{-1}$.

2.2 Preparation of amorphous form of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy)ethyl)(methyl)-amino)cyclohexyl 2-hydroxy-2,2-di(thiophen-2-yl) acetate disaccharinate A solution of saccharine (18 mg, 0.1 mmol) in THF (2 mL) is added over a solution of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy) ethyl)(methyl)-amino)cyclohexyl 2-hydroxy-2,2-di (thiophen-2-yl)acetate (40 mg, 0.5 mmol) in THF (2 mL) at room temperature. The mixture was stirred for 1 hour, and the obtained precipitate was filtered off and dried under vacuum affording 95 mg of the title product (Yield 75%).

2.3 Preparation of Crystalline salt of trans-4-((2-(2-chloro-4-(((R)-2-hydroxy-2-(8-hydroxy-2-oxo-1,2-dihydroquinolin-5-yl)ethylamino)methyl)-5-methoxyphenyl-carbamoyloxy)ethyl)(methyl)-amino)cyclohexyl 2-hydroxy-2,2-di(thiophen-2-yl) acetate disaccharinate from the amorphous form The non-crystalline disaccharinate salt of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy)ethyl)(methyl)-amino)cyclohexyl 2-hydroxy-2,2-di(thiophen-2-yl)acetate (25 mg, 0.031 mmol) was suspended in ethanol (0.5 mL) and stirred at 70° C. for 2 hours. The suspension was allowed to cool to room temperature, and the obtained off-white powder was filtered off and dried overnight under vacuum at 60° C. Yield 10 mg (40%).

2.4 Direct Preparation of crystalline salt of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)(methyl)-amino) cyclohexyl 2-hydroxy-2,2-di(thiophen-2-yl)acetate disaccharinate 225 mg of saccharin are directly added over a hot (70° C.) ethanolic solution of trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyl-oxy)ethyl) (methyl)-amino)cyclohexyl 2-hydroxy-2,2-di(thiophen-2-yl)acetate (500 mg in 3.7 mL of ethanol). The solution was vigorously stirred for 1 hour, turning into a thick off white suspension. The walls of the flask were scratched with a spatula and the suspension was stirred for 15 more minutes. The solid was then filtered off and washed twice with ethanol (2×2 mL), affording 500 mg (70% yield) of a yellowish solid. This saccharinate salt is optionally slurried for 30 minutes in 6 mL of water.

Figure 8:
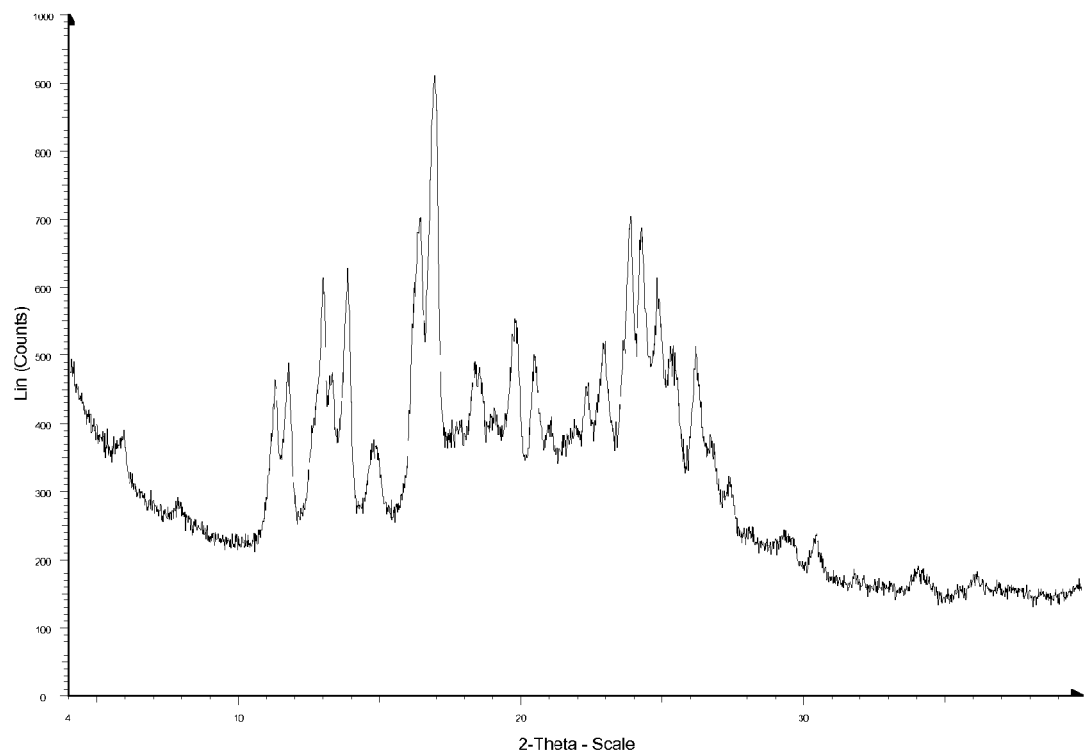
FIG. 8 shows the powder X-ray diffraction (PXRD) pattern for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)(methyl)amino)cyclohexyl 2-hydroxy-2,2-di(thiophen-2-yl)acetate disaccharinate.

FIG. 8 shows the powder X-ray diffraction (PXRD) pattern for the disaccharinate salt. A large number of peaks were observed thus confirming the crystallinity of the salt. The summary of the XRPD angles and relative intensities are given in Table 2.

TABLE 2

| Diffraction Angle (°2θ) | d value (Å) | Relative Intensity (%) |
|---|---|---|
| 11.26 | 7.85 | 51.1 |
| 11.76 | 7.52 | 53.3 |
| 12.95 | 6.83 | 67.5 |
| 13.33 | 6.64 | 52.1 |
| 13.82 | 6.40 | 69.4 |
| 14.81 | 5.98 | 41.5 |
| 16.41 | 5.40 | 77.4 |
| 16.94 | 5.23 | 100 |
| 17.78 | 4.98 | 44.3 |
| 18.36 | 4.83 | 54.1 |
| 18.57 | 4.78 | 52.8 |
| 19.06 | 4.65 | 46.1 |
| 19.76 | 4.49 | 60.7 |
| 20.49 | 4.33 | 54.9 |
| 21.04 | 4.22 | 44.2 |
| 21.88 | 4.06 | 44.5 |
| 22.41 | 3.96 | 50.6 |
| 22.96 | 3.87 | 57.4 |
| 23.89 | 3.72 | 77.4 |
| 24.27 | 3.66 | 75.6 |
| 24.82 | 3.58 | 66.2 |
| 25.41 | 3.50 | 56.5 |
| 26.19 | 3.40 | 56.2 |
| 26.74 | 3.33 | 42 |
| 27.38 | 3.25 | 35 |
| 28.23 | 3.16 | 27.4 |

As can be seen form Table 2, the disaccharinate salt of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)(methyl)-amino)cyclohexyl 2-hydroxy-2,2-di(thiophen-2-yl)acetate is characterized by an X-ray powder diffraction (XRPD) pattern having a significant peak at 2θ values of 16.94±0.2, preferably significant peaks at 2θ values of 16.41±0.2, 16.94±0.2 and 23.89±0.2.

Figure 9:
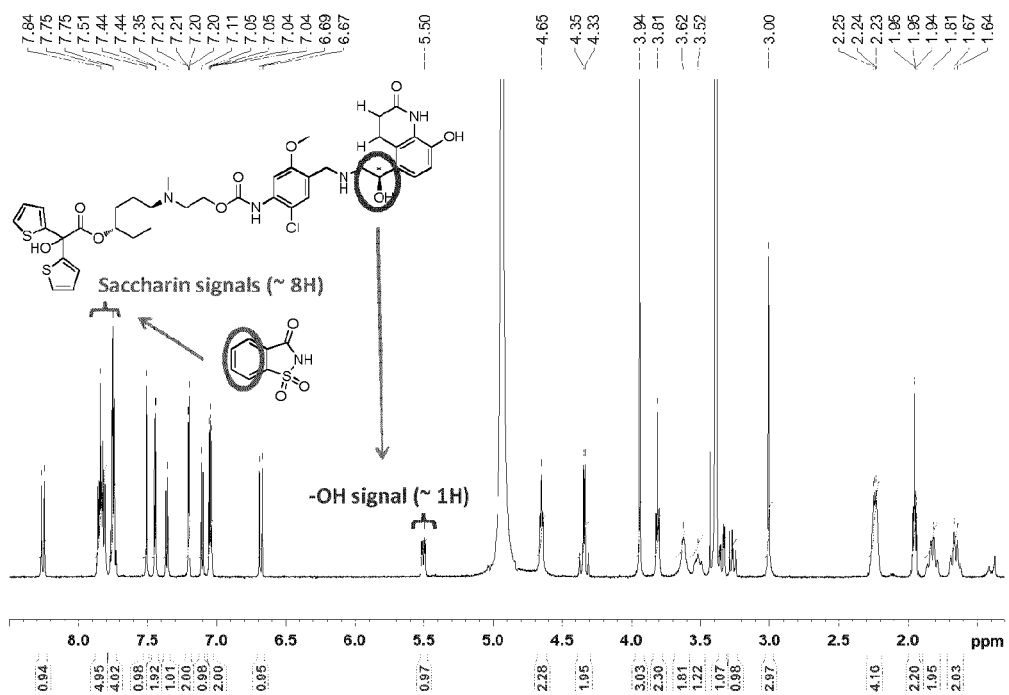
FIG. 9 is the $^1$H-NMR spectrum (500 MHz, d4-methanol) for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate.

FIG. 9 corresponds to the $^1$H-NMR spectrum of the disaccharinate salt. It clearly shows a stoichiometry ratio of 1:2 free base/saccharin, as inferred from the comparison between the integral values of the protons corresponding to the aromatic ring of the saccharin molecule and that of a single proton of the hydroxyl radical of the parent structure.

$^1$H NMR (500 MHz, MeOD-$d_4$) δ ppm): 1.67 (m, 2H), 1.81 (m, 2H), 1.95 (m, 2H), 2.24 (m, 4H), 3.00 (s, 3H), 3.26 (dd, 1H), 3.34 (dd, 1H), 3.52 (m, 1H), 3.62 (m, 2H), 3.81 (m, 2H), 3.94 (s, 3H), 4.34 (m, 2H), 4.65 (m, 2H), 5.50 (dd, 1H), 6.68 (d, 1H), 7.04 (dd, 2H), 7.11 (d, 1H), 7.20 (dd, 2H), 7.36 (d, 1H), 7.44 (dd, 2H), 7.50 (s, 1H), 7.75 (m, 4H), 7.80-7.86 (m, 5H), 8.25 (d, 1H).

Figure 10:
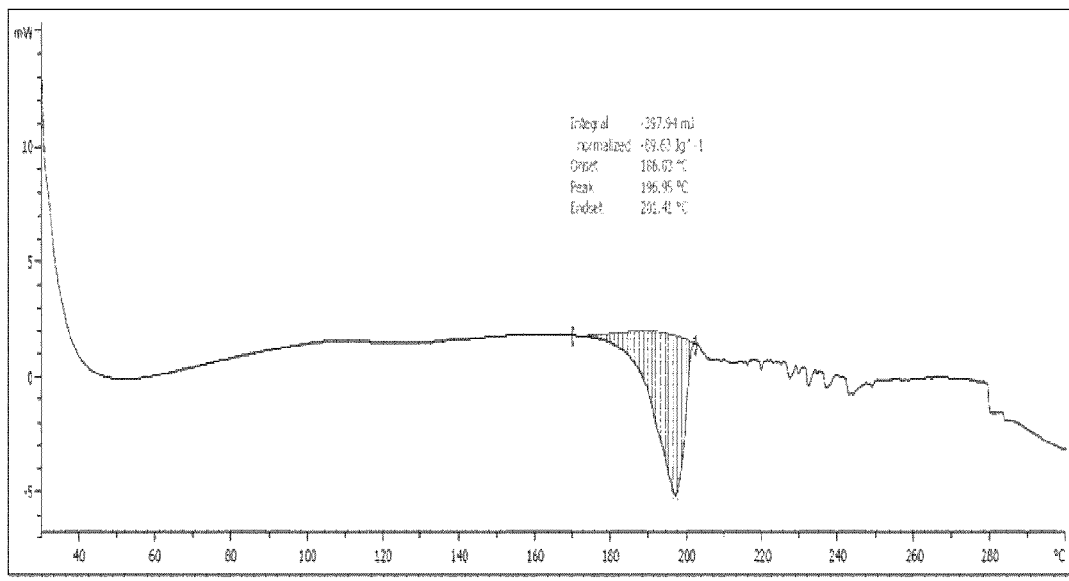
FIG. 10 shows the DSC analysis for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate.

FIG. 10 shows the DSC analysis for the disaccharinate salt showing only an intense endothermic curve with a maximum at 197° C., indicating a possible fusion/decomposition of the salt.

Figure 11:
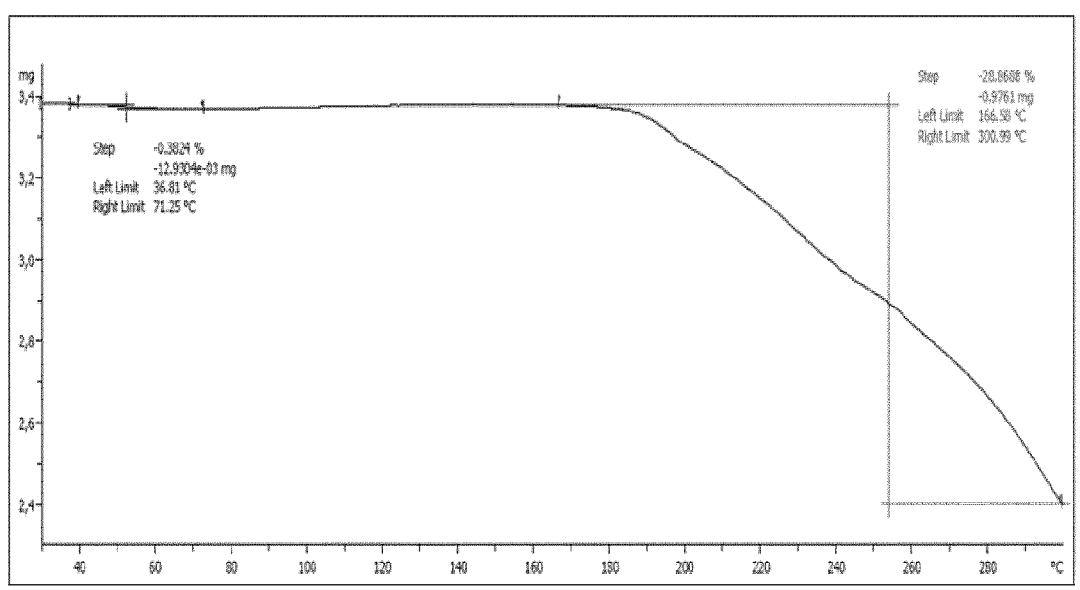
FIG. 11 shows the TG analysis for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate disaccharinate.

FIG. 11 shows the TG analysis for the disaccharinate salt. The spectrum shows a very slight loss of mass between 40 and 80° C. No significant changes are observed until about 160° C., in which the salt decomposes.

Figure 12:
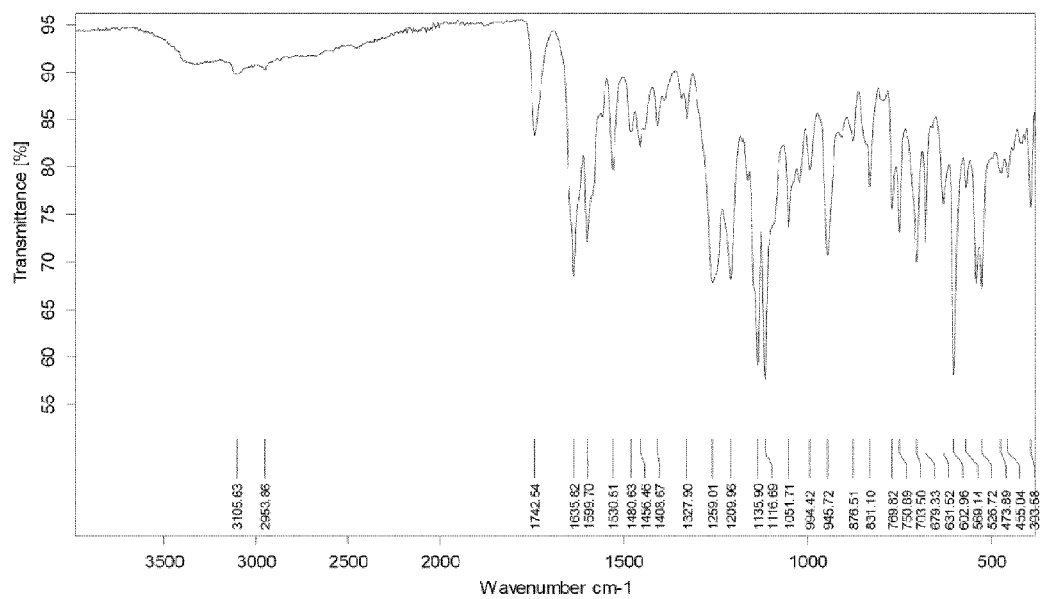
FIG. 12 shows the FTIR spectrum for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy)ethyl)(methyl)amino)cyclohexyl 2-hydroxy-2,2-di(thiophen-2-yl)acetate disaccharinate

FIG. 12 shows the FTIR spectrum for disaccharinate salt. When compared with the free base compound, the infrared spectrum of the disaccharinate has significant differences. A comparison between both spectra is also included in FIG. 12. Significant signal for the disaccharinate appears at: 3106, 2954, 1742, 1636, 1600, 1530, 1456, 1328, 1259, 1210, 1136, 1117, 946, 831, 770, 751, 631, 603 and 527 cm$^{-1}$.

Example 3

Preparation of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)-ethyl)(methyl)amino)cyclohexyl 2-hydroxy-2,2-di(thiophen-2-yl)acetate L-tartrate To a solution of 115 mg of L-tartaric acid in 15 mL of methanol was added a solution 600 mg of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate free base (see preparation 2.1 above) in 20 ml of methanol. The mixture was stirred during 4 hours at room temperature. The resulting precipitate was filtered, and dried under vacuum at 40° C. overnight. Yield 80%.

Figure 13:
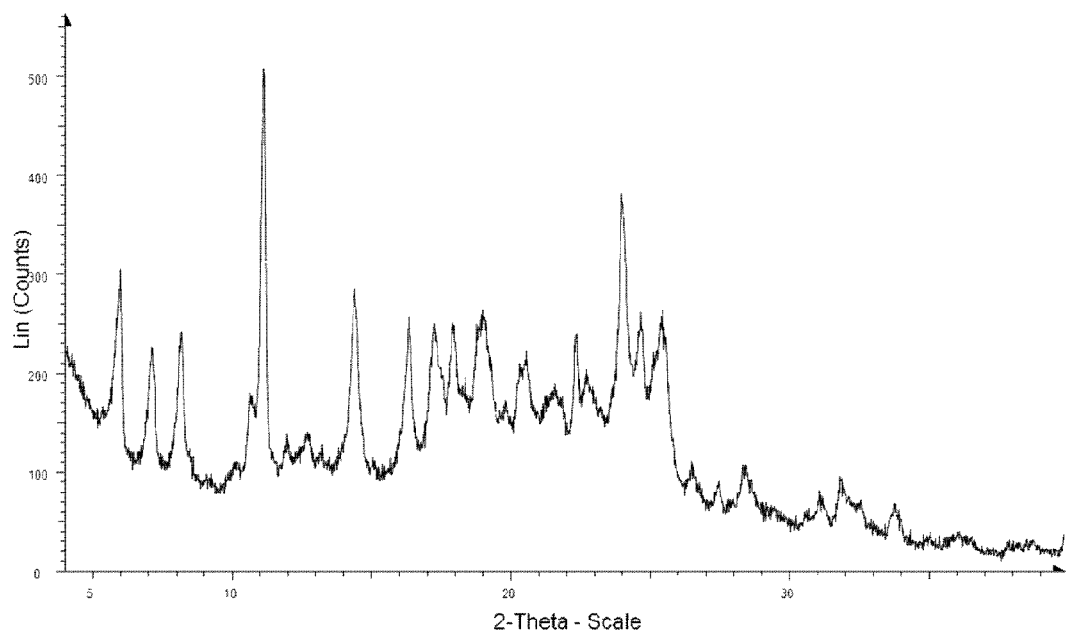
FIG. 13 shows the powder X-ray diffraction (PXRD) pattern for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)(methyl)amino)cyclohexyl 2-hydroxy-2,2-di(thiophen-2-yl)acetate L-tartrate.

FIG. 13 shows the powder X-ray diffraction (PXRD) pattern for the L-tartrate salt. A large number of peaks were observed thus confirming the crystallinity of the salt. The summary of the XRPD angles and relative intensities are given in Table 3.

TABLE 3

| Diffraction Angle (°2θ) | d value (Å) | Relative Intensity (%) |
|---|---|---|
| 5.96 | 14.83 | 64.3 |
| 7.08 | 12.48 | 51.9 |
| 8.10 | 10.90 | 54.7 |
| 10.08 | 8.77 | 32.7 |
| 10.64 | 8.31 | 43.8 |
| 11.10 | 7.96 | 100 |
| 11.95 | 7.40 | 37.5 |
| 12.65 | 6.99 | 37.6 |
| 13.20 | 6.70 | 35 |
| 14.40 | 6.15 | 61.9 |
| 16.32 | 5.43 | 56.9 |
| 17.22 | 5.14 | 55.9 |
| 17.92 | 4.95 | 55.6 |
| 18.91 | 4.69 | 57.2 |
| 19.87 | 4.46 | 42.8 |
| 20.34 | 4.36 | 48.9 |
| 20.52 | 4.33 | 50.9 |
| 21.56 | 4.12 | 44.9 |
| 22.35 | 3.97 | 54.1 |
| 22.73 | 3.91 | 48.3 |
| 24.01 | 3.70 | 78.3 |
| 24.68 | 3.60 | 57.5 |
| 25.41 | 3.50 | 57.4 |
| 26.52 | 3.36 | 32.7 |
| 27.48 | 3.24 | 29 |
| 28.41 | 3.14 | 31.7 |
| 31.09 | 2.87 | 26.9 |
| 31.88 | 2.80 | 29.2 |
| 32.58 | 2.75 | 25.9 |
| 33.80 | 2.65 | 25.4 |

As can be seen form Table 3, the L-tartrate salt of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)(methyl)-amino)cyclohexyl 2-hydroxy-2,2-di(thiophen-2-yl)acetate is characterized by an X-ray powder diffraction (XRPD) pattern having a significant peak at 2θ values of 11.10±0.2, preferably significant peaks at 2θ values of 11.10±0.2 and 24.01±0.2

Figure 14:
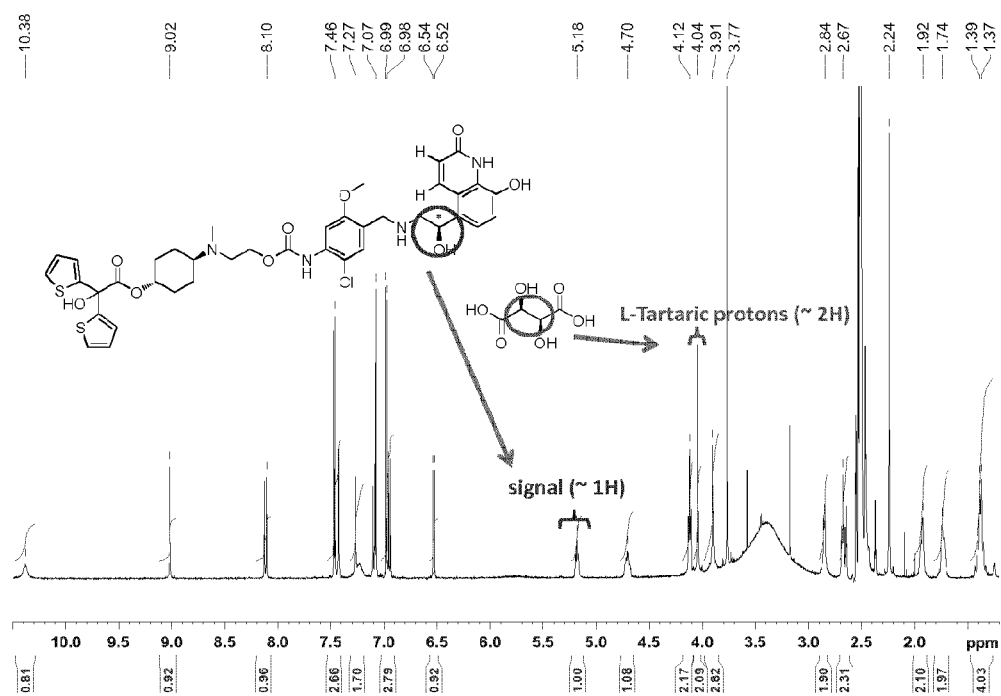
FIG. 14 is the $^1$H-NMR spectrum (500 MHz, d6-DMSO) of trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate L-tartrate.

FIG. 14 corresponds to the ¹H-NMR spectrum of the L-tartrate salt. It clearly shows a stoichiometry ratio of 1:1 free base/L-tartaric acid, as inferred from the comparison between the integral values of the protons corresponding to the hydroxyl radical of the L-tartaric acid molecule and that of a single proton of the hydroxyl radical of the parent structure.

¹H NMR (500 MHz, DMSO-d$_5$) δ (ppm): 1.38 (m, 4H), 1.74 (m, 2H), 1.92 (m, 2H), 2.24 (s, 3H), 2.37 (q, 1H), 2.47 (m, 3H), 2.55 (m, 1H), 2.64 (q, 1H), 2.67 (t, 2H), 2.85 (m, 2H), 3.76 (s, 3H), 3.90 (bs, 2H), 4.04 (bs, 2H), 4.12 (t, 2H), 4.70 (m, 1H), 5.18 (t, 1H), 6.53 (d, 2H), 6.94 (d, 1H), 6.98 (dd, 2H), 7.08 (dd, 2H), 7.10 (d, 1H), 7.27 (bs, 1H), 7.43 (bs, 1H), 7.47 (dd, 2H), 8.11 (d, 1H), 9.02 (s, 1H), 10.40 (bs, 1H).

Figure 15:
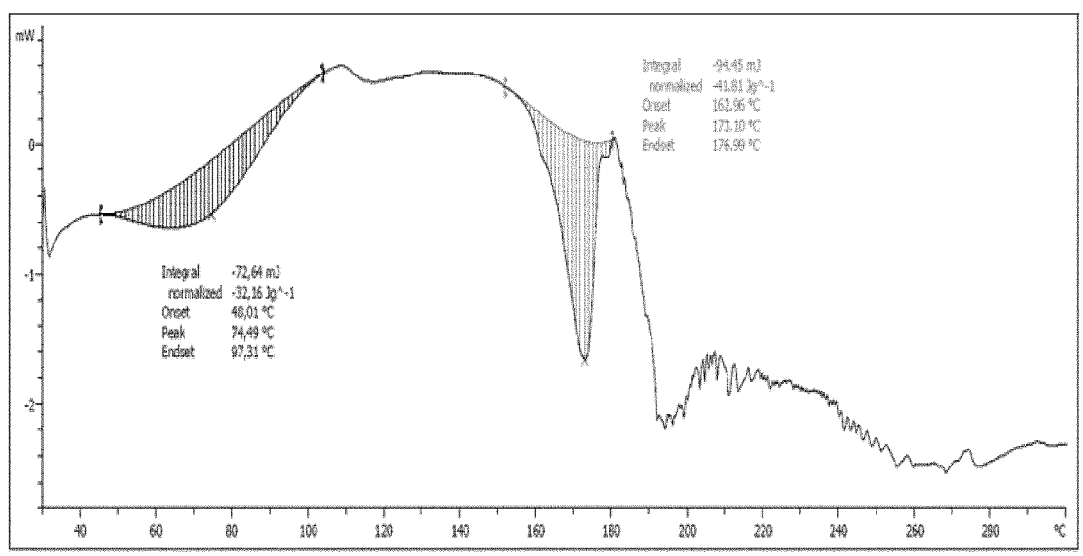
FIG. 15 shows the DSC analysis for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate L-tartrate.

FIG. 15 shows the DSC analysis for the L-tartrate salt showing only an intense endothermic curve with a maximum at 173° C., indicating a possible fusion/decomposition of the salt.

Figure 16:
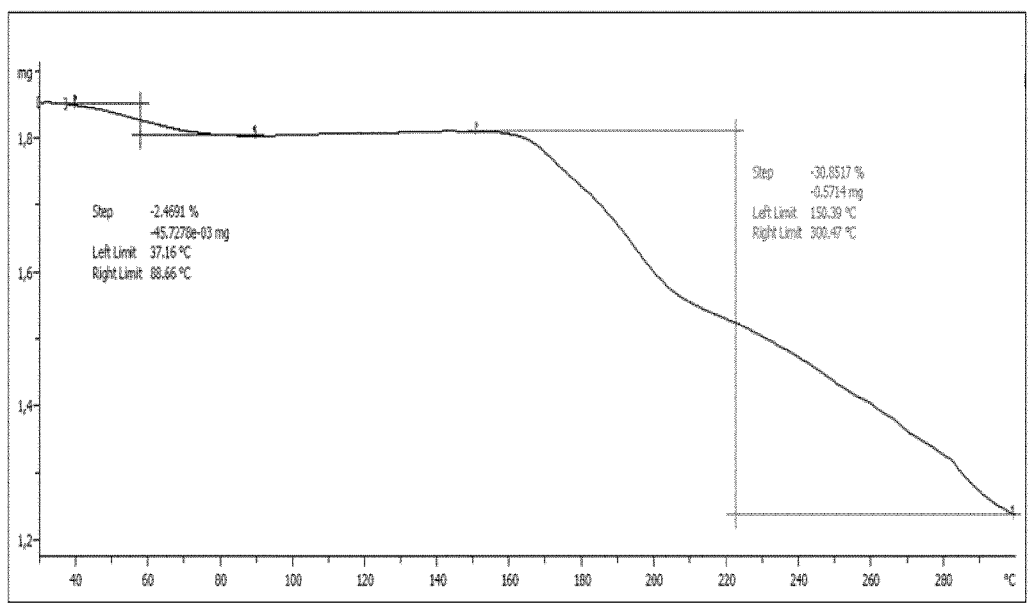
FIG. 16 shows the TG analysis for trans-44(2-(2-chloro-4-(((R)-2-hydroxy-2-(8-hydroxy-2-oxo-1,2-dihydroquinolin-5-yl)ethylamino)methyl)-5-methoxyphenylcarbamoyloxy)ethyl)-(methyl)amino)cyclohexyl 2-hydroxy-2,2-di(thiophen-2-yl)acetate L-tartrate.

FIG. 16 shows the TG analysis for the L-tartrate salt. The spectrum shows a slight loss of mass between 37 and 90° C. probably corresponding to water molecule. No significant changes are observed until about 173° C., in which the salt decomposes.

Figure 17:
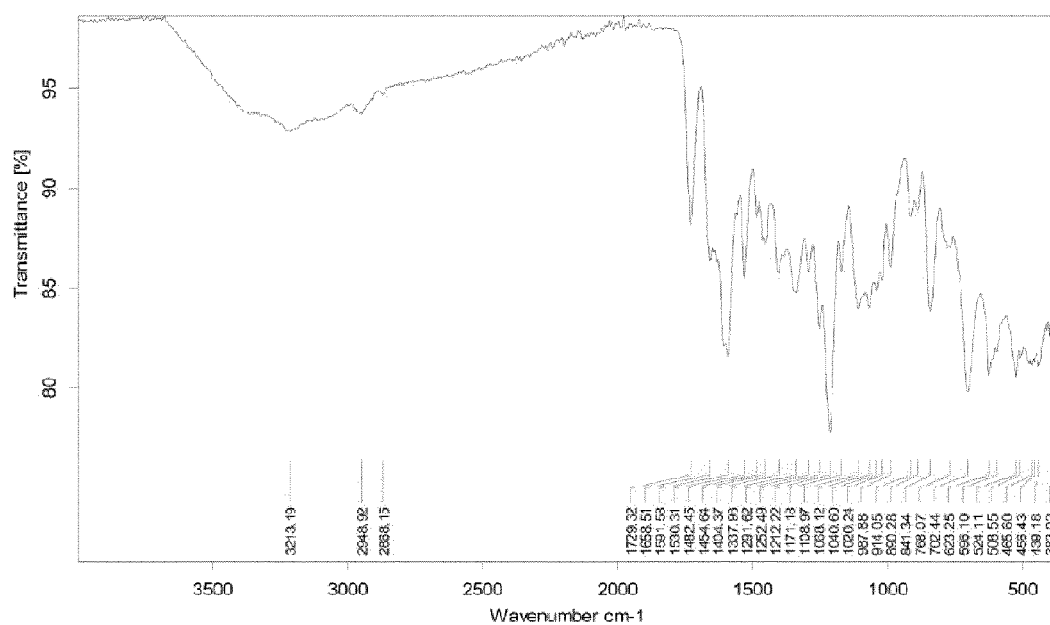
FIG. 17 shows the FTIR spectrum for trans-4-((2-(2-chloro-4-(((R)-2-hydroxy-2-(8-hydroxy-2-oxo-1,2-dihydroquinolin-5-yl)ethylamino)methyl)-5-methoxyphenylcarbamoyl-oxy)ethyl)(methyl)amino)cyclohexyl 2-hydroxy-2,2-di(thiophen-2-yl)acetate L-tartrate.

FIG. 17 shows the FTIR spectrum for L-tartrate salt. Significant signal for the L-tartrate salt appears at: 3213, 2949, 2868, 1729, 1658, 1592, 1530, 1338, 1292, 1212, 1171, 1068, 1041, 841, 702, 623 and 524 cm$^{-1}$.

The following preparations forms are cited as composition (formulation) examples:

Composition Example 1

Formulation Example 1

Formulation for Inhalation with a DPI

| Ingredient | Amount |
| --- | --- |
| L-tartrate salt of trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyloxy)ethyl)-(methyl)amino)cyclohexyl 2-hydroxy-2,2-di(thiophen-2-yl)acetate (micronized) | 15 mg |
| Lactose | 3000 mg |

Formulation Example 2

Formulation for Inhalation with a DPI

| Ingredient | Amount |
| --- | --- |
| trans-4-((2-(2-chloro-4-(((R)-2-hydroxy-2-(8-hydroxy-2-oxo-1,2-dihydroquinolin-5-yl)ethylamino)-methyl)-5-methoxyphenyl-carbamoyloxy)ethyl)-(methyl)amino)-cyclohexyl 2-hydroxy-2,2-di(thiophen-2-yl)acetate disaccharinate (micronized) | 15 mg |
| Lactose | 3000 mg |

Formulation Example 3

Formulation for Inhalation with a DPI

| Ingredient | Amount |
| --- | --- |
| trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexyl hydroxy(di-2-thienyl)acetate ethanedisulfonate (micronized) | 15 mg |
| Lactose | 3000 mg |

Formulation Example 4

Formulation for a MDI

| Ingredient | Amount |
| --- | --- |
| L-tartrate salt of trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyloxy)ethyl)-(methyl)amino)cyclohexyl 2-hydroxy-2,2-di(thiophen-2-yl)acetate (micronized) | 10 g |
| 1,1,1,2,3,3,3-heptafluoro-n-propane | q.s. to 200 ml |

Formulation Example 5

Formulation for a MDI

| Ingredient | Amount |
| --- | --- |
| trans-4-((2-(2-chloro-4-(((R)-2-hydroxy-2-(8-hydroxy-2-oxo-1,2-dihydroquinolin-5-yl)ethylamino)-methyl)-5-methoxyphenyl-carbamoyloxy)ethyl)-(methyl)amino)-cyclohexyl 2-hydroxy-2,2-di(thiophen-2-yl)acetate disaccharinate (micronized) | 10 g |
| 1,1,1,2,3,3,3-heptafluoro-n-propane | q.s. to 200 ml |

Formulation Example 6

Formulation for a MDI

| Ingredient | Amount |
| --- | --- |
| trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexyl hydroxy(di-2-thienyl)acetate ethanedisulfonate (micronized) | 10 g |
| 1,1,1,2,3,3,3-heptafluoro-n-propane | q.s. to 200 ml |

The invention claimed is:

1. A pharmaceutically acceptable crystalline addition salt of (i) a sulfonic, a hydroxycarboxylic acid, a sulfimide derivative, or a pharmaceutically acceptable solvate thereof and (ii) a 2-amino-1-hydroxyethyl-8-hydroxyquinolin-2 (1H)-one derivative of formula (I), or pharmaceutically acceptable solvates thereof,

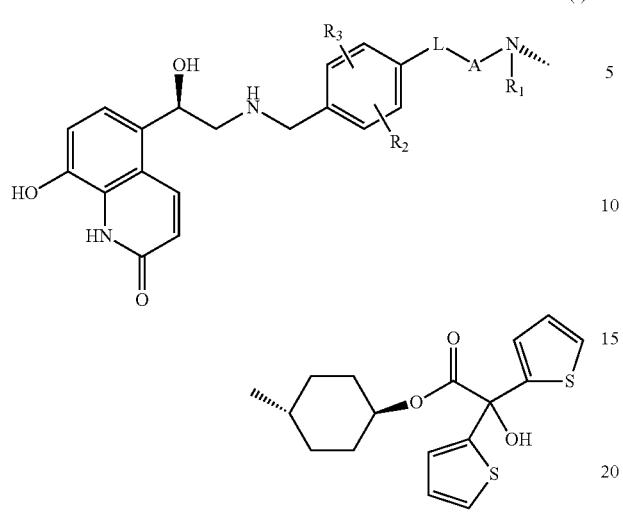

(I)

wherein:
R₁ is a methyl group,
R₂ is a methoxy group, and R₃ is a chlorine atom,
A is an ethylene group,
L is chosen from —NH(CO)—, or —NH(CO)O— group, wherein when L is —NH(CO)O—, the nitrogen atom is bound to the phenylene substituent and the oxygen atom is bound to the A substituent.

2. The salt according to claim 1, chosen from:
trans-4-((3-(2-chloro-4-(((2R)-2-hydroxy-2-(8-hydroxy-2-oxo-1,2-dihydroquinolin-5-yl)ethylamino)methyl)-5-methoxyphenylamino)-3-oxopropyl)(methyl)amino)-cyclohexyl hydroxy(di-2-thienyl)acetate ethanedisulfonate,
trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyloxy)ethyl)-(methyl)amino)-cyclohexyl 2-hydroxy-2,2-di(thiophen-2-yl)acetate disaccharinate,
L-tartrate salt of trans-4-((2-(2-chloro-4-(((R)-2-hydroxy-2-(8-hydroxy-2-oxo-1,2-dihydroquinolin-5-yl)ethylamino)-methyl)-5-methoxyphenylcarbamoyloxy)ethyl)-(methyl)amino)cyclohexyl 2-hydroxy-2,2-di(thiophen-2-yl)acetate,
or a pharmaceutically acceptable solvate thereof.

3. A pharmaceutical composition comprising a therapeutically effective amount of the salt according to claim 1 and a pharmaceutically acceptable carrier.

4. The pharmaceutical composition according to claim 3, wherein the composition is formulated for administration by inhalation as a dry powder.

5. The pharmaceutical composition according to claim 3, further comprising a therapeutically effective amount of at least one additional therapeutic agent.

6. The pharmaceutical composition according to claim 5, wherein the at least one additional therapeutic agent is chosen from:
(a) corticosteroids, or glucocorticoids,
(b) antihistamines,
(c) chemokine receptor antagonists,
(e) CRth2 antagonists,
(f) leukotriene receptor antagonists,
(g) JAK inhibitors,
(h) Syk inhibitors,
(i) phosdiesterase IV inhibitors,
(j) p38 Inhibitors,
(k) PKC inhibitors,
(l) 5-lipoxygenase activating protein inhibitors,
(m) 5-lipoxygenase inhibitors,
(n) CYSLTR1 antagonists,
(o) CYSLTR2 antagonists,
(p) BLT1 antagonists,
(q) BLT2 antagonists,
(r) thromboxane A2 antagonists,
(s) DP1 receptor antagonists,
(t) DP1 receptor agonists,
(u) IP receptor agonists,
(v) Anti-IgE,
(w) IL5 antibody,
(x) leukotriene formation inhibitors,
(y) decongestants,
(z) mucolytics,
(aa) antitussives,
(bb) analgesics, or
(cc) expectorants.

7. The combination comprising a salt according to claim 1 and at least one additional therapeutic agent chosen from:
(a) corticosteroids, or glucocorticoids,
(b) antihistamines,
(c) chemokine receptor antagonists,
(e) CRth2 antagonists,
(f) leukotriene receptor antagonists,
(g) JAK inhibitors,
(h) Syk inhibitors,
(i) phosdiesterase IV inhibitors,
(j) p38 Inhibitors,
(k) PKC inhibitors,
(l) 5-lipoxygenase activating protein inhibitors,
(m) 5-lipoxygenase inhibitors,
(n) CYSLTR1 antagonists,
(o) CYSLTR2 antagonists,
(p) BLT1 antagonists,
(q) BLT2 antagonists,
(r) thromboxane A2 antagonists,
(s) DP1 receptor antagonists,
(t) DP1 receptor agonists,
(u) IP receptor agonists,
(v) Anti-IgE,
(w) IL5 antibody,
(x) leukotriene formation inhibitors,
(y) decongestants,
(z) mucolytics,
(aa) antitussives,
(bb) analgesics, or
(cc) expectorants.

8. A method of treating a pathological condition or disease associated with both β2 adrenergic receptor agonist and M3 antimuscarinic activities, wherein the pathological condition or disease is chosen from asthma or chronic obstructive pulmonary disease, the method comprising administering to a patient in need thereof the salt according to claims 1 and 2.

9. The pharmaceutical composition according to claim 4, further comprising a therapeutically effective amount of at least one additional therapeutic agent.

10. A method of treating a pathological condition or disease associated with both β2 adrenergic receptor agonist and M3 antimuscarinic activities, wherein the pathological condition or disease is chosen from asthma or chronic obstructive pulmonary disease, the method comprising administering to a patient in need thereof the pharmaceutical composition according to claim 3.

11. A method of treating a pathological condition or disease associated with both β2 adrenergic receptor agonist and M3 antimuscarinic activities, wherein the pathological condition or disease is chosen from asthma or chronic obstructive pulmonary disease, the method comprising administering to a patient in need thereof the combination according to claim 7.

* * * * *